US012369871B2

(12) United States Patent
Sasaki et al.

(10) Patent No.: US 12,369,871 B2
(45) Date of Patent: Jul. 29, 2025

(54) X-RAY DIAGNOSTIC APPARATUS

(71) Applicant: CANON MEDICAL SYSTEMS CORPORATION, Otawara (JP)

(72) Inventors: Sho Sasaki, Utsunomiya (JP); Ryoichi Nagae, Nasushiobara (JP); Masanori Matsumoto, Nasushiobara (JP); Yoshiyasu Hayashi, Nasushiobara (JP); Shumpei Ohashi, Otawara (JP); Tomoki Fujito, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 433 days.

(21) Appl. No.: 17/100,240

(22) Filed: Nov. 20, 2020

(65) Prior Publication Data

US 2021/0145386 A1 May 20, 2021

(30) Foreign Application Priority Data

Nov. 20, 2019  (JP) .................. 2019-209392

(51) Int. Cl.
*A61B 6/46* (2024.01)
*A61B 6/00* (2024.01)
(Continued)

(52) U.S. Cl.
CPC .............. *A61B 6/463* (2013.01); *A61B 6/467* (2013.01); *A61B 6/487* (2013.01); *G06F 3/0482* (2013.01);
(Continued)

(58) Field of Classification Search
CPC ......... A61B 6/462; A61B 6/461; A61B 6/464; A61B 6/465; A61B 6/466; A61B 6/463;
(Continued)

(56) References Cited

U.S. PATENT DOCUMENTS 9,661,729 B2 * 5/2017 Arima .................... A61B 6/468
2005/0259116 A1 * 11/2005 Araoka .................. G06T 19/00
345/619
(Continued)

FOREIGN PATENT DOCUMENTS

JP   2000-262506 A   9/2000
JP   2014-210053 A   11/2014
(Continued)

OTHER PUBLICATIONS

Translation of JP-2018143880 (Year: 2018).*
(Continued)

*Primary Examiner* — David J Makiya
*Assistant Examiner* — Soorena Kefayati
(74) *Attorney, Agent, or Firm* — Oblon, McClelland, Maier & Neustadt, L.L.P.

(57) ABSTRACT

An X-ray diagnostic apparatus according to an embodiment includes a storage, an imaging equipment, a display, an input interface, and processing circuitry. The storage memorizes medical images. The imaging equipment includes an X-ray tube configured to emit X-rays toward a subject and a detector configured to detect X-rays emitted from the X-ray tube. The display displays a plurality of medical images including X-ray images captured by the imaging equipment. The input interface accepts an operation instructing storage of a medical image displayed on the display. The processing circuitry identifies a medical image associated with a last-executed, targeted operation, among targeted operations related to any of medical images displayed on the display, and, when the input interface has accepted an operation instructing storage of a medical image displayed on the display, causes the storage to memorize the identified medical image.

21 Claims, 11 Drawing Sheets

(51) Int. Cl.
  *G06F 3/0482* (2013.01)
  *H04N 5/32* (2023.01)
  *H04N 5/76* (2006.01)
  *H04N 7/18* (2006.01)
  *H04N 23/30* (2023.01)

(52) U.S. Cl.
  CPC ............. *H04N 5/32* (2013.01); *H04N 5/76* (2013.01); *H04N 7/181* (2013.01); *H04N 23/30* (2023.01); *A61B 6/4441* (2013.01)

(58) Field of Classification Search
  CPC ......... A61B 6/467; A61B 6/487; A61B 6/548; A61B 6/566; A61B 6/4441; G06F 3/0482; H04N 23/30; H04N 5/32; H04N 5/76; H04N 5/77; H04N 7/181
  See application file for complete search history.

(56) References Cited

U.S. PATENT DOCUMENTS

| | | | |
|---|---|---|---|
| 2008/0166070 A1* | 7/2008 | Kariathungal | G16H 30/40 382/305 |
| 2009/0019400 A1* | 1/2009 | Matsumoto | G06F 8/34 715/840 |
| 2012/0027178 A1* | 2/2012 | Mabini | G16H 30/20 715/764 |
| 2012/0128129 A1* | 5/2012 | Nishii | A61B 6/5205 378/98 |
| 2012/0183191 A1* | 7/2012 | Nakamura | G16H 30/40 382/128 |
| 2012/0287131 A1* | 11/2012 | Matsuzaki | A61B 6/5241 345/426 |
| 2013/0034280 A1* | 2/2013 | Bernhardt | A61B 6/545 382/128 |
| 2013/0093781 A1* | 4/2013 | Suzuki | G16H 30/40 345/581 |
| 2013/0230136 A1* | 9/2013 | Sakaguchi | H04N 13/128 345/419 |
| 2013/0249903 A1* | 9/2013 | Isokawa | G16H 15/00 345/419 |
| 2013/0342577 A1* | 12/2013 | Wang | A61B 6/461 345/634 |
| 2014/0071132 A1* | 3/2014 | Noshi | G16H 50/20 345/427 |
| 2014/0133632 A1* | 5/2014 | Wakai | A61B 6/44 378/98 |
| 2014/0149910 A1* | 5/2014 | Lee | G06F 3/0484 715/771 |
| 2014/0229883 A1* | 8/2014 | Tsukijishin | A61B 6/461 715/773 |
| 2014/0321614 A1* | 10/2014 | Yamada | A61B 6/467 378/62 |
| 2015/0015572 A1* | 1/2015 | Izumo | G06T 19/00 345/419 |
| 2015/0063542 A1* | 3/2015 | Park | A61B 6/542 378/62 |
| 2015/0073257 A1* | 3/2015 | Muraoka | A61B 6/5264 600/407 |
| 2015/0157280 A1* | 6/2015 | Itai | A61B 6/469 600/407 |
| 2015/0178885 A1* | 6/2015 | Kwon | A61B 6/461 345/646 |
| 2015/0265233 A1* | 9/2015 | Aoyagi | G06F 3/1446 345/635 |
| 2015/0317434 A1* | 11/2015 | Kondo | A61B 6/463 705/3 |
| 2015/0317452 A1* | 11/2015 | Kozuka | G06F 3/04842 705/2 |
| 2015/0356271 A1* | 12/2015 | Kozuka | A61B 6/563 705/2 |
| 2015/0363053 A1* | 12/2015 | Aoyama | G16H 30/40 715/838 |
| 2015/0363054 A1* | 12/2015 | Sekiguchi | G06F 3/04883 715/838 |
| 2016/0063183 A1* | 3/2016 | Shimizu | A61B 6/485 705/2 |
| 2016/0073986 A1* | 3/2016 | Saito | A61B 6/469 378/98.2 |
| 2016/0078596 A1* | 3/2016 | Ohashi | A61B 6/566 378/62 |
| 2016/0081646 A1* | 3/2016 | Yoda | A61B 6/032 378/4 |
| 2016/0128795 A1* | 5/2016 | Kozuka | G16H 30/20 715/771 |
| 2016/0143602 A1* | 5/2016 | Hiroike | A61B 6/5258 378/91 |
| 2016/0199015 A1* | 7/2016 | Li | H04N 13/398 348/51 |
| 2016/0210410 A1* | 7/2016 | Oda | G16H 10/60 |
| 2016/0232668 A1* | 8/2016 | Ishiraha | A61B 6/032 |
| 2016/0296182 A1 | 10/2016 | Neumann | |
| 2016/0364837 A1* | 12/2016 | Aoyama | G06T 11/60 |
| 2017/0112439 A1 | 4/2017 | Dubin et al. | |
| 2018/0020997 A1* | 1/2018 | Fujita | A61B 6/4233 378/62 |
| 2018/0055461 A1* | 3/2018 | Iizuka | A61B 6/035 |
| 2018/0218785 A1* | 8/2018 | Sugiyama | A61B 6/037 |
| 2018/0303343 A1 | 10/2018 | Dubin et al. | |
| 2019/0028657 A1* | 1/2019 | Katsushima | G16H 40/63 |
| 2019/0313996 A1* | 10/2019 | Park | A61B 6/5294 |
| 2019/0392940 A1* | 12/2019 | Suzuki | A61B 6/032 |

FOREIGN PATENT DOCUMENTS

| | | |
|---|---|---|
| JP | 2016-510418 A | 4/2016 |
| JP | 2018143880 A * | 9/2018 |
| JP | 2018-530804 A | 10/2018 |
| JP | 2019-500176 A | 1/2019 |
| WO | WO 2013/046983 A1 | 4/2013 |
| WO | WO 2014/127379 A1 | 8/2014 |
| WO | WO 2017/011814 A1 | 1/2017 |

OTHER PUBLICATIONS

Office Action issued May 9, 2023, in corresponding Japanese Patent Application No. 2019-209392, 6 pages.

Japanese Office Action issued Nov. 28, 2023 in Japanese Patent Application No. 2019-209392, 7 pages.

* cited by examiner

FIG.10
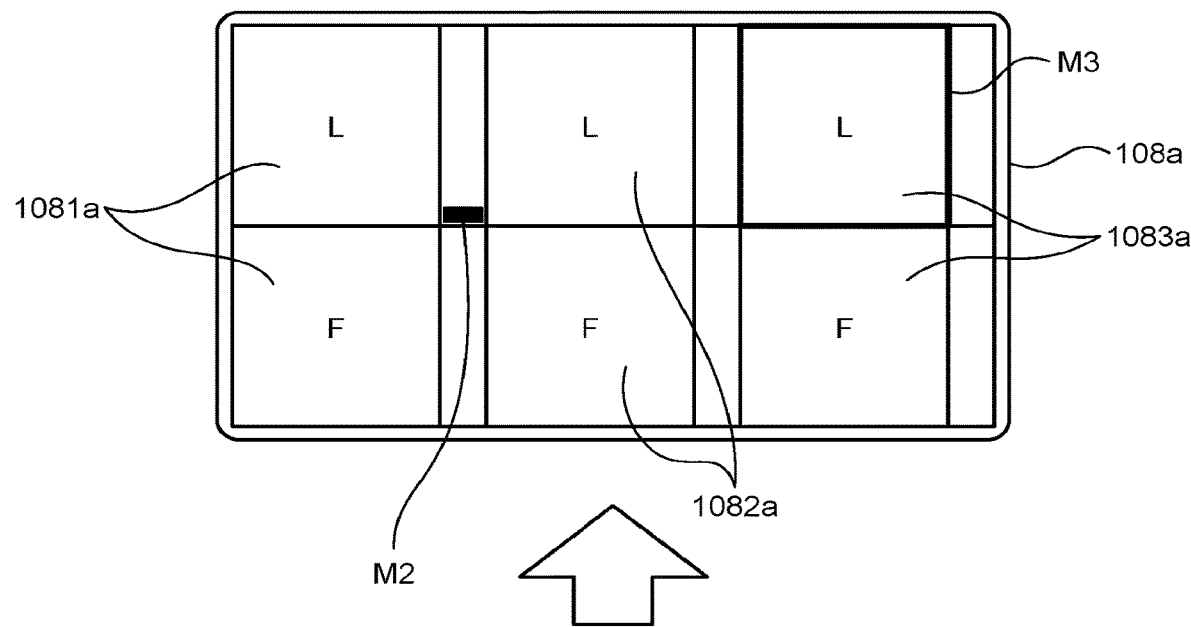
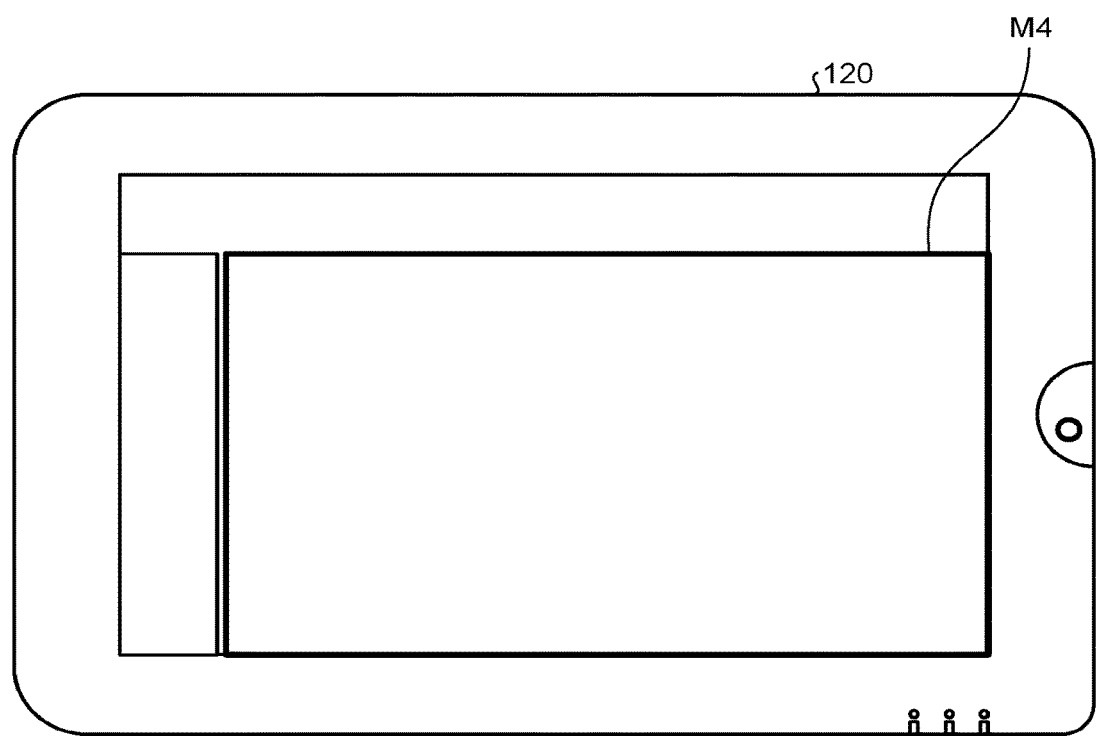

X-RAY DIAGNOSTIC APPARATUS

CROSS-REFERENCE TO RELATED APPLICATIONS

This application is based upon and claims the benefit of priority from Japanese Patent Application No. 2019-209392, filed on Nov. 20, 2019; the entire contents of which are incorporated herein by reference.

FIELD

Embodiments described herein relate generally to an X-ray diagnostic apparatus.

BACKGROUND

Conventionally, an X-ray diagnostic apparatus has a still image storage function used to store still images. The function is used to store images for reference purposes during a medical operation, and to store desired images to be kept as evidence. Here, at least two types of still image storage buttons are provided and used to store still images. One is a button that is used to store one frame of a video that has been captured and collected. The other is a button that is used to store an X-ray image displayed on a monitor during fluoroscopy. Some X-ray diagnostic apparatuses each include a plurality of monitors that each display possible-target images to be stored, and the corresponding number of buttons.

BRIEF DESCRIPTION OF THE DRAWINGS

FIG. 10 is a view of example processing to be performed by an output function according to the second embodiment;

DETAILED DESCRIPTION

Figure 1A:
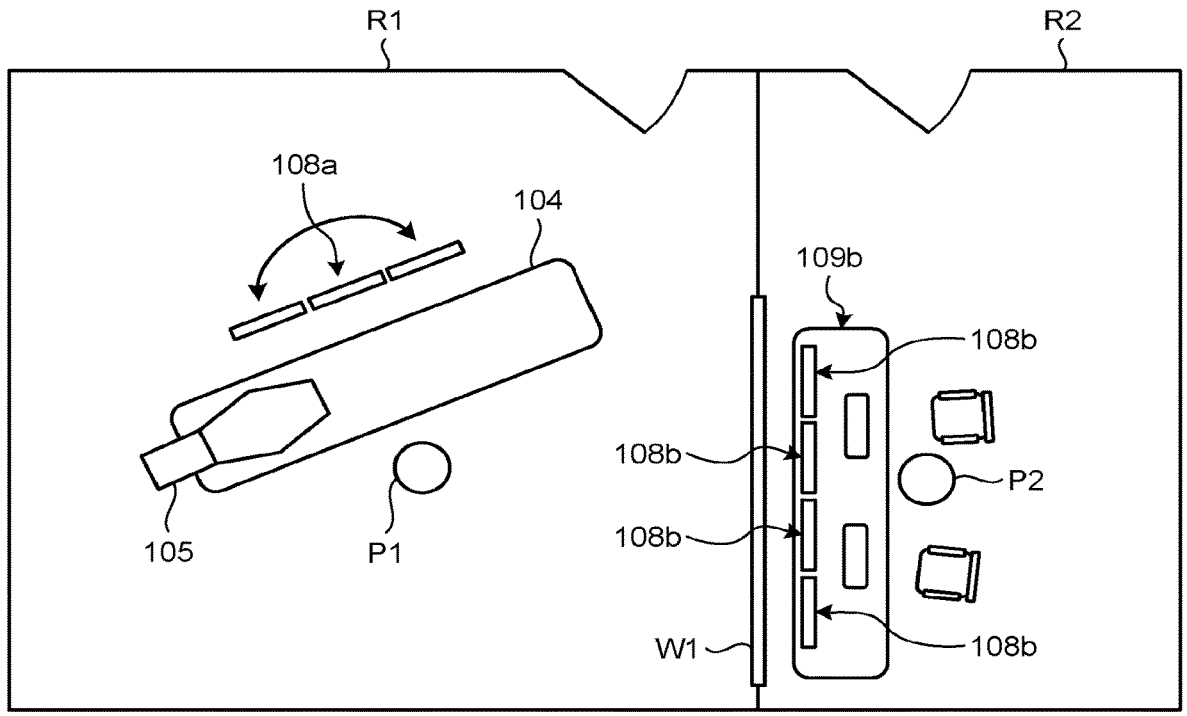
FIG. 1A is a view of an illustrative example of an X-ray diagnostic apparatus according to a first embodiment.

According to an embodiment, an X-ray diagnostic apparatus includes a storage, an imaging equipment, a display, an input interface, and processing circuitry. The storage is configured to memorize medical images. The imaging equipment includes an X-ray tube configured to emit X-rays toward a subject and a detector configured to detect X-rays emitted from the X-ray tube. The display is configured to display a plurality of medical images including X-ray images captured by the imaging equipment. The input interface is configured to accept an operation instructing storage of a medical image displayed on the display. The processing circuitry is configured to identify a medical image associated with a last-executed, targeted operation, among targeted operations related to any of medical images displayed on the display, and, when the input interface has accepted an operation instructing storage of a medical image displayed on the display, to cause the storage to memorize the identified medical image.

Embodiments of an X-ray diagnostic apparatus will now be described in detail with reference to the accompanying drawings. The X-ray diagnostic apparatus according to the present application is not limited by the embodiments described below. It is possible to combine the embodiments with other embodiments and prior arts within a range where no inconsistency arises in processing contents. It is to be noted that like reference numerals designate identical or corresponding components throughout the below description and the accompanying drawings. Duplicated descriptions are thus omitted.

FIRST EMBODIMENT

Figure 1B:
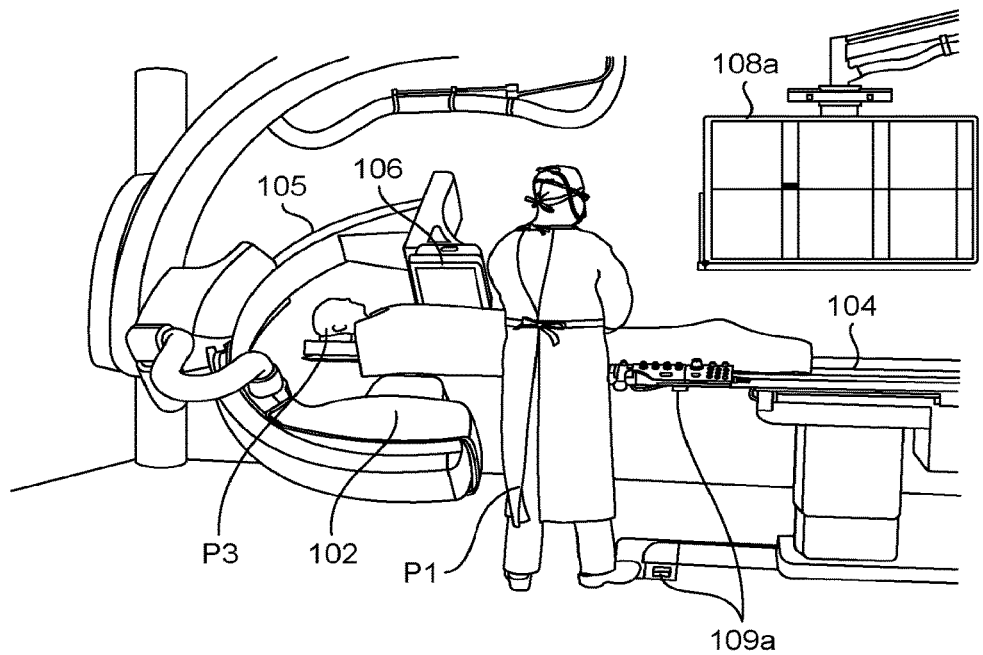
FIG. 1B is a view of an illustrative example of the X-ray diagnostic apparatus according to the first embodiment.

With reference to FIGS. 1A and 1B, an example of an X-ray diagnostic apparatus according to a first embodiment will first be described. FIGS. 1A and 1B are views of an illustrative example of the X-ray diagnostic apparatus according to the first embodiment. For example, as illustrated in FIG. 1A, an apparatus main body of the X-ray diagnostic apparatus includes a C arm 105 and a tabletop 104. The apparatus main body is disposed in an examination room R1 used for a diagnosis and a medical treatment of circulatory system including brain and heart, for example. In an observation room R2 illustrated in FIG. 1A, an operation terminal used to execute an operation for controlling the apparatus main body is disposed. Here, the apparatus main body disposed in the examination room R1 includes, as illustrated in FIG. 1B, examination room input interfaces 109a including a table-side console and a foot switch, for example, to be operated by a medical doctor P1 performing manipulation.

In the examination room R1 and the observation room R2, respectively, a plurality of examination room monitors 108a and a plurality of observation room monitors 108b, for example, are provided. For example, the examination room monitors 108a are observed by a medical operator (the medical doctor) performing manipulation, and by nurses, for example. The observation room monitors 108b are observed by a device operator who executes an operation for controlling the apparatus main body. In an example case, while observing fluoroscopic images displayed on the examination room monitors 108a in the examination room R1, the medical doctor P1 performing manipulation moves the C arm 105 that holds an X-ray tube 102 and an X-ray detector 106 to perform a medical treatment in a brain blood vessel of a subject P3, for example. For example, in the observation room R2, a technician P2, for example, follows an instruction from the medical doctor P1 to operate an observation room input interface 109b while observing the observation room monitors 108b to adjust parameters and to perform various kinds of processing on images, for example. A window W1 is provided on a partition wall that partitions the examination room R1 and the observation room R2, for example, allowing, via the window W1, the examination room R1 and the observation room R2 to be both internally confirmed.

Figure 2:
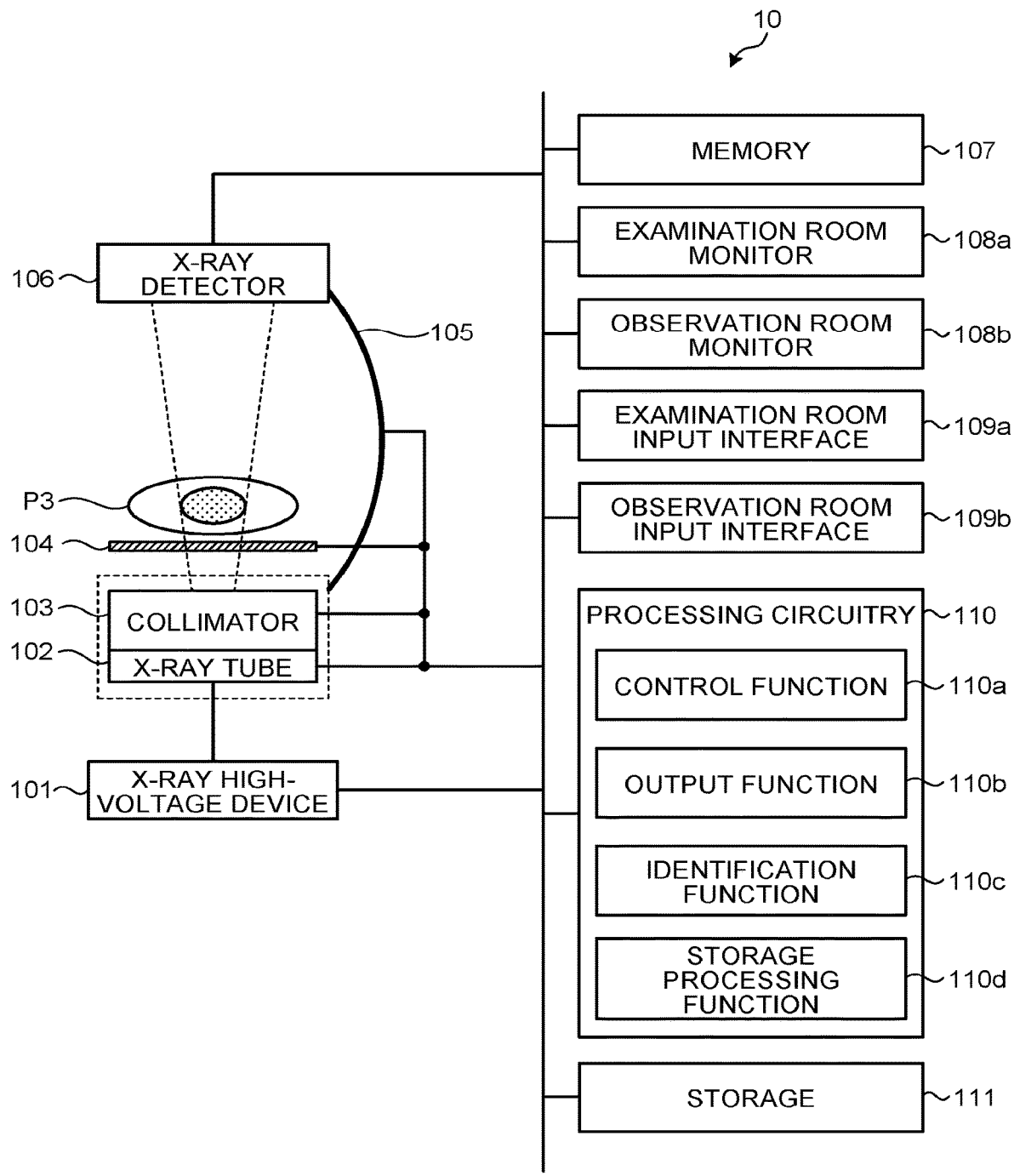
FIG. 2 is a block diagram of a configuration example of the X-ray diagnostic apparatus according to the first embodiment.

Next, a configuration of the X-ray diagnostic apparatus according to the first embodiment will be described. FIG. 2 is a block diagram of a configuration example of an X-ray diagnostic apparatus 10 according to the first embodiment. As illustrated in FIG. 2, the X-ray diagnostic apparatus 10 includes an X-ray high-voltage device 101, the X-ray tube 102, a collimator 103, the tabletop 104, the C arm 105, the X-ray detector 106, a memory 107, the examination room monitors 108a, the observation room monitors 108b, the examination room input interfaces 109a, the observation room input interface 109b, processing circuitry 110, and a storage 111.

Here, the X-ray tube 102 and the X-ray detector 106 constitute an example of an imaging portion. The storage 111 constitutes an example of a memory portion. The examination room monitors 108a and the observation room monitors 108b constitute an example of a display portion. The examination room input interfaces 109a and the observation room input interface 109b constitute an example of a storage instruction acceptance portion.

Under the control by the processing circuitry 110, the X-ray high-voltage device 101 supplies a high voltage to the X-ray tube 102. For example, the X-ray high-voltage device 101 includes an electric circuit including a transformer and a rectifier, for example, and further includes a high-voltage generator configured to generate a high voltage to be applied to the X-ray tube 102, and an X-ray controller configured to control an output voltage in accordance with X-rays that the X-ray tube 102 emits. For the high-voltage generator, a transformer style or an inverter style may be adopted.

The X-ray tube 102 is a vacuum tube including a negative electrode (a filament) from which thermal electrons are generated, and a positive electrode (a target) with which the thermal electrons collide to generate X-rays. The X-ray tube 102 uses the high voltage that the X-ray high-voltage device 101 supplies to allow thermal electrons to exit from the negative electrode and to reach the positive electrode to generate X-rays.

The collimator 103 includes an X-ray limiter configured to limit an area to be irradiated with X-rays that the X-ray tube 102 generates, and a filter configured to adjust the X-rays that the X-ray tube 102 emits.

The X-ray limiter in the collimator 103 has four slidable limiting blades, for example. The X-ray limiter causes the limiting blades to slide to limit X-rays that the X-ray tube 102 generates to cause a subject P to be irradiated with the X-rays. Here, the limiting blades are plate members made of lead, for example, and, to adjust an area to be irradiated with X-rays, are provided around an X-ray emission port of the X-ray tube 102.

The filter in the collimator 103 changes radiation quality of X-rays that pass through the subject P, in accordance with a material and a thickness, to reduce a radiation dose with respect to the subject P and to improve image quality of X-ray image data, so as to reduce soft X-ray components that the subject P easily absorbs and to reduce high energy components that lower in contrast the X-ray image data. The filter further changes a radiation dose of X-rays and an area to be irradiated with the X-rays, in accordance with the material, the thickness, and a position, for example, to allow the X-rays to attenuate to attain a predetermined distribution of the X-rays emitted from the X-ray tube 102 toward the subject P.

For example, the collimator 103 includes a drive mechanism including a motor and an actuator, for example, to cause the drive mechanism to operate under the control by the processing circuitry 110, described later, to control X-rays to be emitted. For example, when a drive voltage is applied to the drive mechanism in accordance with a control signal that the collimator 103 accepts from the processing circuitry 110, the collimator 103 adjusts an opening degree of the limiting blades of the X-ray limiter to control an area in which the subject P is to be irradiated with X-rays. For example, when a drive voltage is applied to the drive mechanism in accordance with a control signal that the collimator 103 accepts from the processing circuitry 110, the collimator 103 further adjusts a position of the filter to control a distribution of a radiation dose of X-rays with which the subject P is irradiated.

The tabletop 104 is a bed on which the subject P lies, and is disposed on a non-illustrated table. The subject P is not included in the X-ray diagnostic apparatus 10. For example, the table includes a drive mechanism including a motor and an actuator, for example, to cause the drive mechanism to operate under the control by the processing circuitry 110, described later, to control a movement and an inclination of the tabletop 104. For example, when a drive voltage is applied to the drive mechanism in accordance with a control signal accepted from the processing circuitry 110, the table causes the tabletop 104 to move and incline.

The X-ray tube 102 and the collimator 103, and the X-ray detector 106 are held by the C arm 105 so as to face to each other and to allow the subject P to lie therebetween. For example, the C arm 105 includes a drive mechanism including a motor and an actuator, for example, to cause the drive mechanism to operate under the control by the processing circuitry 110, described later, to rotate and move. For example, when a drive voltage is applied to the drive mechanism in accordance with a control signal accepted from the processing circuitry 110, the C arm 105 causes the X-ray tube 102 and the collimator 103, and the X-ray detector 106 to rotate and move relative to the subject P to control a position and an angle at which the subject P is irradiated with X-rays. The example case where the X-ray diagnostic apparatus 10 has a single plane has been described with reference to FIG. 2. However, the embodiment is not limited to the example case. An example case where the X-ray diagnostic apparatus 10 has a biplane may also be applicable.

The X-ray detector 106 is an X-ray flat panel detector (FPD) including detection elements arranged in a matrix, for example. The X-ray detector 106 detects X-rays emitted from the X-ray tube 102 and passed through the subject P, and outputs, to the processing circuitry 110, a detection signal corresponding to an amount of the detected X-rays. The X-ray detector 106 may be an indirect conversion-type detector including a grid, a scintillator array, and an optical sensor array, or a direct conversion-type detector including semiconductor elements configured to convert incident X-rays into an electric signal.

The memory 107 is achieved, for example, by a semiconductor memory element such as a random access memory (RAM). The memory 107 temporarily memorizes a result of processing performed by the processing circuitry 110. For example, the memory 107 accepts and temporarily memorizes various kinds of data such as X-ray image data collected by the processing circuitry 110. Here, the X-ray image data according to the present application includes a detection signal detected by the X-ray detector 106, projection data generated based on the detection signal, and an X-ray image generated based on the projection data. The various kinds of data that the memory 107 memorizes is memorized and stored in the storage 111 in response to storage processing performed by the processing circuitry 110.

The storage 111 is achieved, for example, by a semiconductor memory element, such as a flash memory, a hard disk, or an optical disk. The storage 111 accepts and memorizes various kinds of data such as X-ray image data collected by the processing circuitry 110. Specifically, the storage 111 memorizes and stores various kinds of data accepted in response to the storage processing performed by the processing circuitry 110. For example, the storage 111 memorizes still images and videos, for example, which have been generated in accordance with processing performed by the processing circuitry 110, and which have undergone the storage processing executed by the processing circuitry 110. Still images and videos will be described later in detail.

The storage 111 further memorizes computer programs that the processing circuitry 110 reads and executes, and that correspond to various kinds of functions. The storage 111 may be achieved by a server group (cloud) coupled, via a network, to the X-ray diagnostic apparatus 10.

The examination room monitors 108a and the observation room monitors 108b display various kinds of information. For example, the examination room monitors 108a and the observation room monitors 108b display, under the control by the processing circuitry 110, graphical user interfaces (GUIs) for each accepting an instruction provided by the device operator, and various kinds of X-ray images. The examination room monitors 108a and the observation room monitors 108b further display medical images received from an external apparatus. Here, the examination room monitors 108a and the observation room monitors 108b can each display a plurality of medical images. For example, the examination room monitors 108a and the observation room monitors 108b can each simultaneously display a plurality of X-ray images and a plurality of medical images received from an external apparatus.

In an example case, where the examination room monitors 108a and the observation room monitors 108b each include a plurality of monitors, the monitors can each display medical images. For example, the examination room monitors 108a and the observation room monitors 108b respectively are large screen monitors, making it possible to each display a plurality of medical images in a plurality of partitioned regions. The examination room monitors 108a and the observation room monitors 108b are liquid crystal displays or cathode ray tube (CRT) displays, for example. Either ones of the examination room monitors 108a and the observation room monitors 108b may each include a plurality of monitors, and the others may be large screen monitors.

The examination room input interfaces 109a and the observation room input interface 109b accept various kinds of input operations from the device operator, convert the accepted input operations into electric signals, and output the electric signals to the processing circuitry 110. For example, the examination room input interfaces 109a and the observation room input interface 109b are achieved, for example, by a mouse, a keyboard, a trackball, switches, buttons, a joystick, a touch pad having an operation face to be touched for an input operation, a touch screen in which a display screen and a touch pad are integrated with each other, a non-contact input circuit using an optical sensor, and a voice input circuit. For example, the examination room input interfaces 109a include a table-side console disposed next to the tabletop 104, for example. For example, the observation room input interface 109b is an input interface of any kind, which is disposed on an operation console in the observation room R2.

Here, the examination room input interfaces 109a and the observation room input interface 109b each include a storage button used to store a medical image displayed on each of the examination room monitors 108a and the observation room monitors 108b. That is, the examination room input interfaces 109a each include the storage button used to store a medical image displayed on each of the examination room monitors 108a in the examination room R1. The observation room input interface 109b includes the storage button used to store a medical image displayed on each of the observation room monitors 108b.

The examination room input interfaces 109a and the observation room input interface 109b each include an active marker switching button used to switch an active marker, and special buttons used to execute special functions linked beforehand to the monitors, for example. The active marker, the active marker switching button, and the special buttons will be described later in detail.

The processing circuitry 110 executes a control function 110a, an output function 110b, an identification function 110c, and a storage processing function 110d to wholly control operation of the X-ray diagnostic apparatus 10. Here, the control function 110a is an example of an operation target setting portion. The output function 110b is an example of a display control portion. The identification function 110c is an example of a target identification portion. The storage processing function 110d is an example of a storage portion.

For example, the processing circuitry 110 reads and executes, from the storage 111, a computer program corresponding to the control function 110a to collect X-ray image data. For example, the control function 110a controls the X-ray high-voltage device 101 to adjust a voltage to be supplied to the X-ray tube 102 to control an amount of X-rays with which the subject P is irradiated, and to perform on/off controls.

For example, the control function 110a controls operation of the collimator 103 to adjust an opening degree of the limiting blades that the X-ray limiter includes to control an area of which the subject P is to be irradiated with X-rays. Specifically, the control function 110a causes the limiting blades in the X-ray limiter to slide, changing as desired a shape, a size, and a position of an opening that the limiting blades form. For example, the control function 110a causes the limiting blades to slide and move so that only a region of interest (ROI) that is set, via an input interface 109, by a user is irradiated with X-rays. That is, the control function 110a causes the limiting blades to slide and move so as to allow the ROI to have a shape and a size at a position, all of which are designated by the user.

The control function 110a controls operation of the collimator 103 to adjust a position of the filter to control a distribution of a radiation dose of X-rays. For example, the control function 110a causes the filter to move to a position that is set, via the input interface 109, by the user to control a distribution of a radiation dose of X-rays. The control function 110a controls operation of the C arm 105 to cause the C arm 105 to rotate or move. For example, the control function 110a controls operation of the table to cause the tabletop 104 to move or incline.

The control function 110a generates projection data based on a detection signal received from the X-ray detector 106, and stores the generated projection data in the memory 107. The control function 110a performs various kinds of image processing on the projection data that the memory 107 memorizes to generate an X-ray image. The control function 110a executes, on the X-ray image, for example, noise reduction processing and correction of scattered rays with an image processing filter. The control function 110a uses projection data collected through rotography to reconfigure volume data to generate an X-ray image from the reconfigured volume data. The control function 110a sets targets to be operated via the examination room input interfaces 109a and the observation room input interface 109b.

The processing circuitry 110 reads and executes, from the storage 111, a computer program corresponding to the output function 110b to cause the examination room monitors 108a and the observation room monitors 108b to display the GUIs and X-ray images. For example, the output function 110b reads, from the memory 107, the X-ray images collected under the control by the control function 110a, and causes the examination room monitors 108a and the observation room monitors 108b to display the X-ray images. The output function 110b causes the examination room monitors 108a and the observation room monitors 108b to display still images and videos, for example, stored in the storage 111, in response to an operation by the device operator.

The identification function 110c identifies a target medical image to be stored, on the basis of an operation by the device operator. The storage processing function 110d causes the storage 111 to memorize the medical image identified by the identification function 110c. The processing to be performed by the identification function 110c and the storage processing function 110d will be described later in detail.

The overall configuration of the X-ray diagnostic apparatus 10 has been describe above. The configuration leads to improved operability of the X-ray diagnostic apparatus 10 through the processing that the processing circuitry 110 performs. Specifically, improved operability of the X-ray diagnostic apparatus 10 is achieved through identifying a target medical image to be memorized, on the basis of an operation by the device operator, and causing the storage 111 to memorize the identified medical image.

As described above, the X-ray diagnostic apparatus includes a still image storage function used to store images for reference purposes during a medical operation, and to store desired images to be kept as evidence, for example. As for operability of a still image storage button to be used to use the still image storage function, a case where at least two types of still image storage buttons are provided will be described. In such a case, immediately determining which of still image storage buttons should be used, among two or more types of storage buttons, is burdensome and stressful for the device operator.

Figure 3:
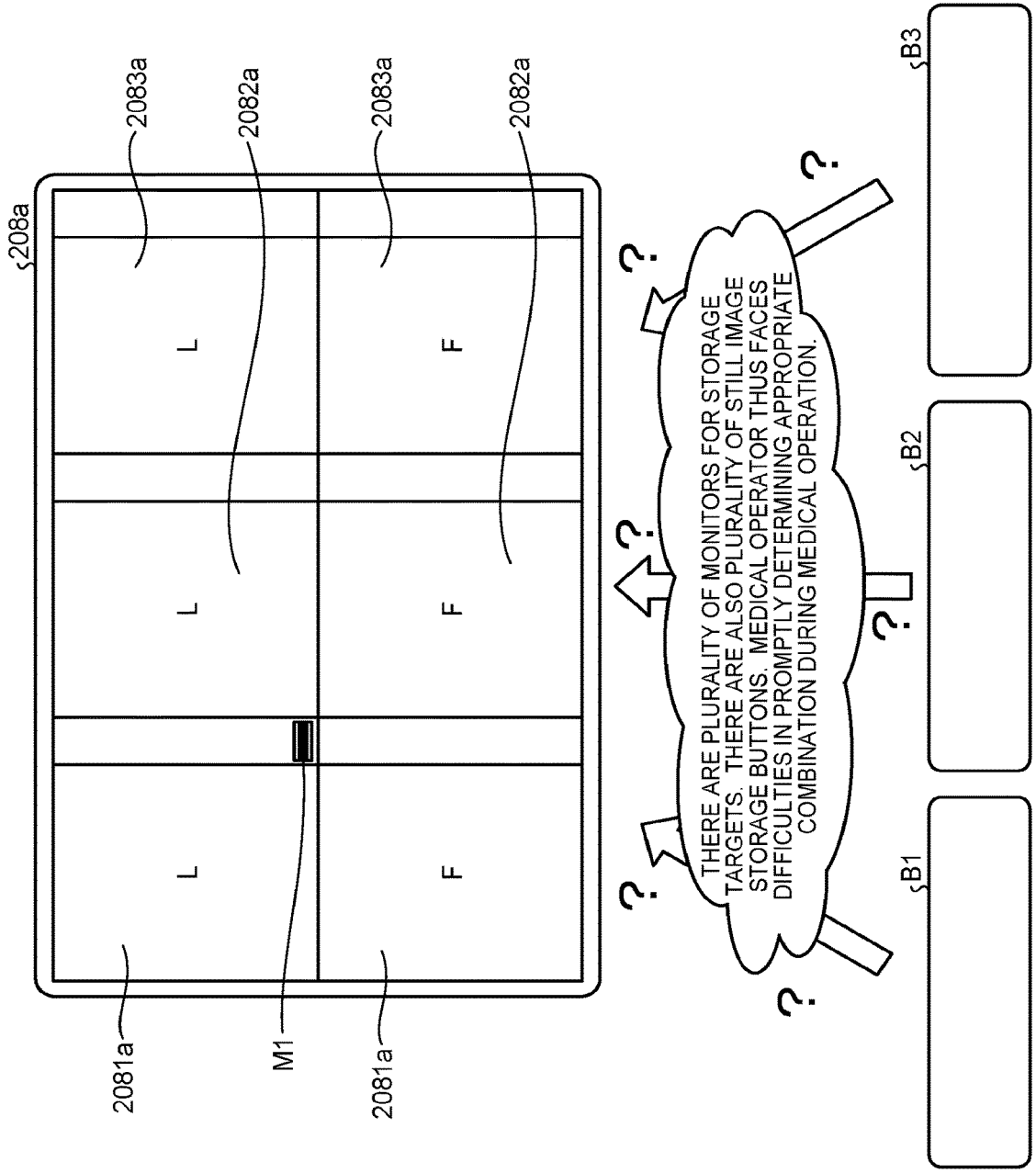
FIG. 3 is a view of an illustrative example of a storage operation by using a plurality of still image storage buttons according to the first embodiment.

FIG. 3 is a view of an illustrative example of a storage operation by using a plurality of still image storage buttons according to the first embodiment. Here, FIG. 3 illustrates a case where, as an examination room monitor 208a, an L (Lateral) side and an F (Frontal) side of a biplane each include a live monitor 2081a, a reference monitor 2082a, and an additional monitor 2083a. FIG. 3 illustrates the case where an active marker M1 is used to select a target to be stored as a still image or a target to be image-processed, for example. The active marker M1 is added on a monitor that displays an image. The image displayed on the monitor (an active monitor) added with the active marker M1 represents a target to be stored as a still image or a target to be image-processed, for example. That is, the medical operator selects with the active marker M1 a monitor (image) from which a still image is to be stored or for which image processing is to be performed, for example, before pressing down the still image storage button or executing an operation for image processing. Here, the device operator can also select with the active marker M1 a monitor that has already displayed a target image to be stored as a still image or a target image to be image-processed, or can select with the active marker M1 a monitor that has not yet displayed an image.

Here, a position of the active marker M1 is changed by the active marker switching button (not illustrated). For example, the examination room monitor 208a illustrated in FIG. 3 includes regions, in each of which the active marker M1 is to be displayed, respectively, in the live monitor 2081a, the reference monitor 2082a, and the additional monitor 2083a on the L side, and the live monitor 2081a, the reference monitor 2082a, and the additional monitor 2083a on the F side. The device operator presses down the active marker switching button to switch the position of the active marker M1. In an example case, each time the active marker switching button is pressed down, the position of the active marker M1 is changed in the order of the live monitor 2081a, the reference monitor 2082a, and the additional monitor 2083a on the L side, and the live monitor 2081a, the reference monitor 2082a, and the additional monitor 2083a on the F side. The device operator presses down the active marker switching button to select an active monitor from the monitors. The device operator then presses down one of the storage buttons to cause a still image to be stored.

FIG. 3 illustrates the case where the storage buttons include, for example, a fluoroscopic image storage button B1 used to store a fluoroscopic image, a reference image storage button B2 used to store a reference image, and an evidence image storage button B3 used to store an evidence image that is an image to be kept as evidence. To store a still image during a medical operation in such a situation, the device operator first presses down the active marker switching button to move the position of the active marker M1 to select an active monitor. The device operator then selects and presses down one of the storage buttons, which corresponds to a medical image that the device operator wants to store as a still image.

However, as illustrated in FIG. 3, when there are a plurality of monitors, and also a plurality of storage buttons, the device operator (the medical operator) faces difficulties in promptly determining an appropriate combination during a medical operation. The X-ray diagnostic apparatus 10 according to the present application identifies a target medical image to be stored on the basis of an operation executed by the device operator to control and store the identified medical image in response to a single button operation, achieving improved operability. Specifically, the X-ray diagnostic apparatus 10 identifies, as a target to be stored, a medical image associated with an operation finally executed by the device operator (immediately before pressing down one of the storage buttons), in the course of an operation related to storage of a medical image, among operations executed by the device operator. This feature eliminates the use of the active marker to select an active monitor, and the use of one of the storage buttons per image, achieving improved operability. That is, the device operator is required to select neither a monitor nor a button before pressing down the storage button. By simply pressing down the storage button, the device operator can cause the X-ray diagnostic apparatus 10 to execute storage processing for a desired medical image. Details of the processing performed by the X-ray diagnostic apparatus 10 will be described below.

The identification function 110c identifies a medical image associated with a last-executed, targeted operation, among targeted operations related to any of a plurality of medical images displayed on the examination room monitors 108a and the observation room monitors 108b. Specifically, the identification function 110c identifies a medical image associated with a targeted operation including at least one operation among operations related to generation, editing, and display of a medical image to be displayed on each of the examination room monitors 108a and the observation room monitors 108b, among operations executed by the device operator.

Here, in a case where various kinds of operations are to be executed, the control function 110a sets a target to be operated in response to an operation performed by the device operator via each of the examination room input interfaces 109a and the observation room input interface 109b. For example, the control function 110a sets, upon the acceptance of an operation of selecting a monitor, the selected monitor as a target to be operated in relation to generation, editing, and display, for example, of a medical image. For example, the control function 110a sets, upon the acceptance of an operation of selecting a displayed medical image, the selected medical image as a target to be operated.

Operations related to generation of a medical image include, for example, operations related to parametric imaging that generates, from a video of contrast X-ray images, a color image in which pixels have colors corresponding to values of blood flow parameters including a blood flow arrival time. Operations related to editing of a medical image include, for example, operations related to various kinds of image processing. Operations related to display of a medical image include, for example, operations related to play, stop, frame advance, and cut switching of a video. Here, cut switching refers to an operation of switching a target video to be displayed.

A medical image that the device operator wants to store during a medical operation is an image to which a certain operation has been executed. For example, a case where a fluoroscopic image is to be stored as a target corresponds to a state where, after the device operator has operated a fluoroscopy switch (e.g., the foot switch), a fluoroscopic image is displayed. For example, to store one of a plurality of captured images as a reference image, the device operator causes a monitor to display each of the captured images in a frame advance manner to select a desired, captured image. An image having undergone measurement processing or editing processing, for example, serves as a target medical image to be stored. As described above, an image on which the device operator has executed a certain operation serves as a target medical image to be stored.

The identification function 110c identifies, as a target to be stored, a medical image associated with an operation finally executed by the device operator, in the course of an operation related to storage of a medical image, among operations executed by the device operator. An operation finally executed by the device operator will be referred to as a last operation.

For example, the identification function 110c identifies, when a last operation corresponds to pressing down of the fluoroscopy switch, a fluoroscopic image as a target to be stored. For example, the identification function 110c identifies, when a last operation corresponds to a measurement on a medical image, the medical image having undergone the measurement as a target to be stored. For example, the identification function 110c identifies, when a last operation corresponds to a case where a video has been frame-advanced, the frame-advancing has been stopped, and a medical image has been displayed, the video as a target to be stored. For example, the identification function 110c identifies, when a last operation corresponds to stopping of a video being played, the video as a target to be stored.

Here, the identification function 110c can identify a medical image associated with a last-executed, targeted operation, on the basis of priority set in accordance with a kind of the medical image. That is, the identification function 110c identifies a target medical image to be stored on the basis of priority set beforehand for each medical image to be operated by the device operator. For example, in a case where an order of the priority is set as "fluoroscopic image>captured image>medical image received from external apparatus", the identification function 110c always identifies, during fluoroscopy, a fluoroscopic image as a target to be stored. For example, the identification function 110c always identifies, while the device operator is pressing down the fluoroscopy switch, a fluoroscopic image as a target to be stored, and continuously identifies, even when an operation for another medical image is then executed, a fluoroscopic image as the target to be stored.

As described above, the identification function 110c identifies a medical image associated with a last operation performed by the device operator as a target image to be stored. Here, a last operation includes, as described above, at least one operation among operations related to generation, editing, and display of a medical image to be displayed on each of the examination room monitors 108a and the observation room monitors 108b, among operations executed by the device operator. That is, it is possible to define beforehand whether each of the operations is regarded as a last operation. For example, all operations related to generation, editing, and display of a medical image may each be regarded as a last operation. A particular operation may not be regarded as a last operation.

In an example case, among operations to cause the examination room monitors 108a to each display a medical image, an operation performed via one of the examination room input interfaces 109a and an operation performed via the observation room input interface 109b may each be regarded as a last operation. That is, among all operations related to generation, editing, and display of a medical image, an operation performed via each of the examination room input interfaces 109a and the observation room input interface 109b is also defined as a last operation.

Among operations to cause the examination room monitors 108a to each display a medical image, an operation performed via each of the examination room input interfaces 109a may be regarded as a last operation. An operation performed via the observation room input interface 109b may not be regarded as a last operation. For example, an operation of displaying a fluoroscopic image may not be defined as a last operation. That is, a fluoroscopic image may not be regarded as a target image to be stored. For example, an operation for a medical image received from an external apparatus may not be defined as a last operation.

Here, a definition of whether an operation is regarded as a last operation may be changed depending on a situation. For example, a definition may be changed per operator. In an example case, it may be defined respectively that, when a medical doctor A takes a role of a device operator, an operation of displaying a fluoroscopic image is regarded as a last operation, and, meanwhile, when a medical doctor B takes a role of a device operator, an operation of displaying a fluoroscopic image is not regarded as a last operation.

It is possible to control and cancel identification by the identification function 110c along with system ON/OFF of the X-ray diagnostic apparatus 10, switching of a protocol, or changing of a display monitor, for example. That is, when one of the operations described above is executed, the identification function 110c deletes information of a medical image identified at this time.

Figure 4:
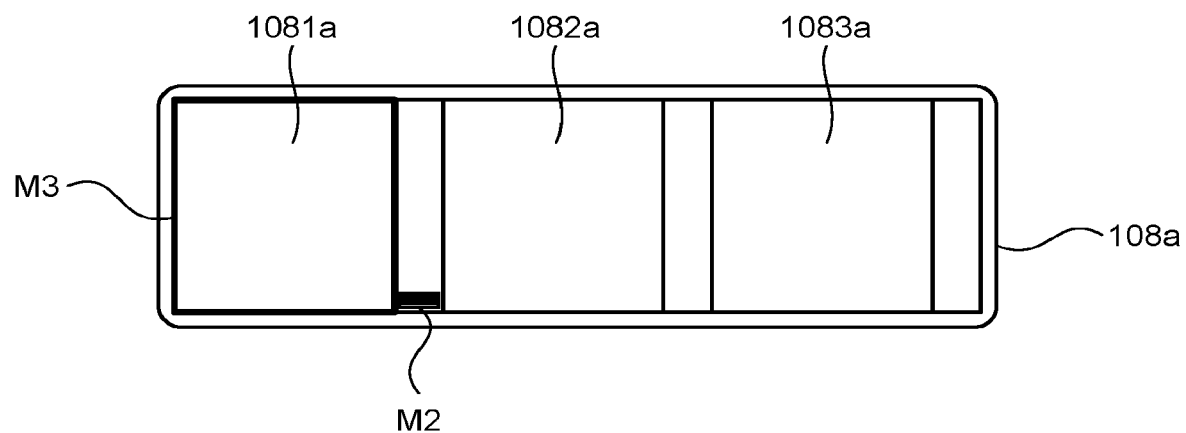
FIG. 4 is a view of example processing to be performed by an output function according to the first embodiment.

As described above, when the identification function 110c identifies a target medical image to be stored, the output function 110b causes the examination room monitors 108a and the observation room monitors 108b to display information allowing the identified medical image to be recognized. FIG. 4 is a view of example processing to be performed by the output function 110b according to the first embodiment. Here, FIG. 4 illustrates an example case where one of the examination room monitors 108a is focused on. In FIG. 4, a live monitor 1081a represents a monitor that displays an X-ray image (e.g., a fluoroscopic image) collected at this time. A reference monitor 1082a represents a monitor that displays a reference image. An additional monitor 1083a represents a monitor that has been added to display more information.

For example, when the device operator operates the fluoroscopy switch, collection of a fluoroscopic image starts, and the identification function 110c identifies the fluoroscopic image as a target image to be stored, the output function 110b causes the live monitor 1081a that displays the fluoroscopic image to display a marker M3, as illustrated in FIG. 4. Therefore, the device operator can confirm at one view that the fluoroscopic image is a present target image to be stored. At this time, the control function 110a has set the live monitor 1081a that displays the marker M3 and the fluoroscopic image as the target to be operated. Here, for example, when the device operator has ceased to operate the fluoroscopy switch, but has performed an operation of causing a reference monitor 1082a to display a reference image, the identification function 110c identifies the reference image as a target image to be stored. In response to the identification, the output function 110b causes to transition the marker M3 being displayed to the reference monitor 1082a. At this time, the control function 110a has set the reference monitor 1082a that displays the marker M3 and the reference image as the target to be operated.

FIG. 4 illustrates the case where the marker M3 is used as information that allows an identified medical image to be recognized. However, the embodiment is not limited to this case. An active marker M2 may be used. In such a case, the output function 110b controls and causes a monitor that displays an identified medical image to display the active marker M2.

As described above, the output function 110b causes to display information allowing the device operator to recognize a medical image identified by the identification function 110c, allowing the device operator to easily confirm the medical image being set as the present target to be stored. In response to an operation performed via one of the examination room input interfaces 109a or the observation room input interface 109b, the output function 110b can cause to change a display position of the marker M3 (or, the active marker M2). That is, if an undesired medical image has been set as a target to be stored, the device operator can operate one of the examination room input interfaces 109a or the observation room input interface 109b to change the position of the marker M3 (or, the active marker M2).

Here, in the X-ray diagnostic apparatus 10 according to the present embodiment, as described above, the examination room input interfaces 109a and the observation room input interface 109b each include the active marker switching button used to move the position of the active marker, and the special buttons used to execute the special functions linked beforehand to the monitors. The active marker switching button is a button used to switch the position of the active marker representing a marker that indicates a target to be operated. For example, each time the device operator presses down the active marker switching button, the position of the active marker moves from the live monitor 1081a, the reference monitor 1082a, to the additional monitor 1083a in order in the examination room monitor 108a.

For example, the device operator presses down the active marker switching button to select a monitor (image) to be served as a target to be operated. The identification function 110c regards the operation as a last operation, and identifies, as a target to be stored, a medical image displayed on the monitor to which the active marker has been moved. As the device operator presses down the active marker switching button, the output function 110b causes the display position of the active marker to move. As described above, the device operator can make a last operation, that is, can use the active marker switching button to move the position of the active marker. The active marker is used to not only select a target to be stored, but also select one of other various kinds of targets to be operated. That is, for various kinds of operations, the device operator can use the active marker to select a target.

The special buttons linked beforehand to the monitors represent buttons to be each pressed down when the device operator uses a certain function. Here, the special buttons are respectively linked to a plurality of display regions (the live monitor 1081a, the reference monitor 1082a, and the additional monitor 1083a) included in the examination room monitor 108a to accept an operation for a medical image displayed on each of the display regions that are linked to the special buttons. The special buttons are examples of operation switches. For example, the examination room input interfaces 109a are each disposed with the special buttons respectively corresponding to play, stop, frame advance, and cut switching, for example, of a video displayed on each of the examination room monitors 108a. One of the buttons is linked to the reference monitor 1082a, for example. When the one of the buttons is pressed down, the reference monitor 1082a is set as a target monitor to be operated. Processing associated with the one of the buttons, which has been pressed down, is executed for an image displayed on the reference monitor 1082a. That is, the special buttons represent buttons each used to execute the special processing on an image displayed on the monitor linked beforehand as a target to be operated.

The identification function 110c regards pressing down of one of the special buttons as a last operation to identify a medical image displayed on the reference monitor 1082a as a target to be stored. Here, even when one of the special buttons is pressed down, the position of the active marker does not move. That is, the output function 110b does not cause the active marker to move to the reference monitor 1082a identified by the identification function 110c, but keeps its present display position. At this time, even though the target to be stored is changed to an image corresponding to the one of the special buttons, the target to be operated without using the special buttons is kept to the image for which the active marker has been displayed. In other words, the control function 110a sets a target to be operated without using the special switch. The active marker sets a target to be operated without using the special buttons. The identification function 110c causes, in accordance with a targeted operation by using one of the special buttons, medical images to transition, one of which is to be identified as a target to be stored. However, the control function 110a does not change the target to be operated, but keeps the target, depending on a targeted operation by using one of the special buttons.

The storage processing function 110d causes, when one of the examination room input interfaces 109a and the observation room input interface 109b accepts an operation instructing storage of a medical image displayed on one of the examination room monitors 108a and the observation room monitors 108b, the storage 111 to memorize the identified medical image. That is, after an operation that is regarded as a last operation is executed, and the storage button on one of the examination room input interfaces 109a or the observation room input interface 109b is pressed down, the storage processing function 110d reads a present image, which is identified from medical images by the identification function 110c, from the memory 107, and causes the storage 111 to store the image. Here, the storage button functions as a storage button for all medical images, and is disposed on each of the examination room input interfaces 109a and the observation room input interface 109b.

For example, after a fluoroscopic image is identified as a target to be stored, and the storage button on one of the examination room input interfaces 109a is pressed down, the storage processing function 110d causes the storage 111 to store, as a still image, the fluoroscopic image displayed when the storage button is pressed down. For example, after a medical image having undergone a measurement is identified as a target to be stored, and the storage button on one of the examination room input interfaces 109a is pressed down, the storage processing function 110d causes the storage 111 to store the medical image displayed when the storage button is pressed down (e.g., the medical image indicated with a measured position or a result of measurement). For example, after a video is identified as a target to be stored, and the storage button on one of the examination room input interfaces 109a is pressed down, the storage processing function 110d causes the storage 111 to store, as a still image, the image displayed when the storage button is pressed down.

Here, the storage processing function 110d can change a type of a storage function in accordance with a kind of an identified medical image. Specifically, the storage processing function 110d changes the type of the storage function for pressing down of the storage button, in accordance with a kind of an identified medical image. For example, the storage processing function 110d changes the type of the storage function to be associated with an operation to be accepted by the storage button, between a case where the identified medical image is a fluoroscopic image and a case where the identified medical image is a captured image.

In an example case, where a fluoroscopic image is identified as a target to be stored, the storage processing function 110d causes, when the storage button is not long-pressed down, but is short-pressed down once, the storage 111 to store, as a still image, the fluoroscopic image displayed when the storage button is pressed down. The storage processing function 110d causes, when the storage button is long-pressed down, the storage 111 to store, as a video, fluoroscopic images collected during a period of the long-pressed down.

When a fluoroscopic image is identified as a target to be stored, and the storage button is pressed down after fluoroscopy, the storage processing function 110d causes the storage 111 to store, as a video, all fluoroscopic images collected during the fluoroscopy. In this case, the storage processing function 110d temporarily memorizes fluoroscopic images collected during the fluoroscopy, and, as the storage button is pressed down after the fluoroscopy, causes the storage 111 to store, as a video, all the fluoroscopic images stored temporarily.

The storage processing function 110d can cause the storage 111 to memorize supplementary information given on an identified medical image, in such a manner that the supplementary information is associated with the identified medical image. Specifically, the storage processing function 110d causes the storage 111 to memorize supplementary information, in such a manner that the supplementary information is associated with a given position on a medical image. As described above, the X-ray diagnostic apparatus 10 identifies a medical image having undergone a measurement, for example, as a target to be stored, and causes the storage 111 to memorize the identified medical image. Here, although the storage processing function 110d can cause, to store in the storage 111 as is, a medical image superimposed with information of measurement (e.g., a position of measurement and a result of measurement), the storage processing function 110d can also cause the storage 111 to separately memorize a medical image and information superimposed on the medical image, respectively, in such a manner that the medical image and the information are still associated with each other.

That is, the storage processing function 110d causes a medical image and information, including a straight line indicating a position of measurement and a result of measurement, for example, superimposed on the medical image to be stored separately, in such a manner that the medical image and the information are associated with each other at a position where the information is superimposed on the medical image. Therefore, to read and display memorized information later, the output function 110b can cause to display a medical image only, or to display a superimposed image on which selected information is only superimposed on the medical image, for example. Supplementary information to be stored, in such a manner that the supplementary information is associated with a medical image, includes not only information regarding a measurement as described above, but also an annotation, a pictogram, and other results of analysis, for example.

Examples of results of analyses superimposed on medical images include, for example, fractional flow reserve (FFR) and instantaneous wave-free ratio (iFR). For example, when an indication based on an index such as FFR or iFR is superimposed on a contrast image identified as a target to be stored, the storage processing function 110d may cause the storage 111 to store as is a displayed image acquired through superimposition, and also stores an image (a contrast image) onto which information is to be superimposed and the information to be superimposed (e.g., FFR or iFR), in such a manner that the image onto which the information is to be superimposed and the information to be superimposed are associated with each other. That is, the storage processing function 110d causes the storage 111 to store a contrast image and information to be superimposed, in such a manner that the contrast image and the information to be superimposed are associated with each other, in addition to information of a position at which the information is to be superimposed on the contrast image (positioning information).

As described above, to store a medical image and supplementary information in such a manner that the medical image and the supplementary information are associated with each other, the storage processing function 110d causes the storage 111 to store a display aspect of when the medical image and the supplementary information are stored as a default setting, for example. Therefore, to display again the image and the supplementary information, the image and the supplementary information can be displayed in an identical manner when the image and the supplementary information have been stored. The display thus promptly presents that there is the supplementary information, making it possible to change later in a desired manner a display aspect including switching ON/OFF of the supplementary information.

Figure 5:
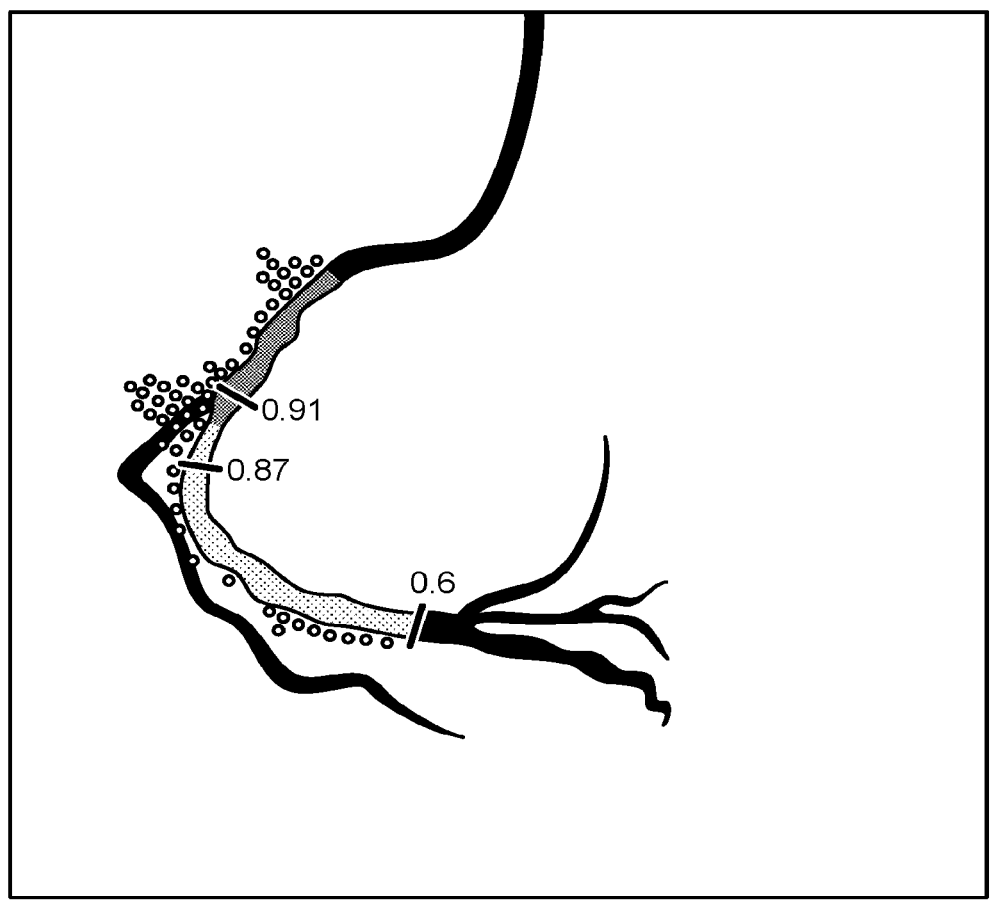
FIG. 5 is a view of example information to be given on a medical image, according to the first embodiment.

FIG. 5 is a view of example information to be given on a medical image, according to the first embodiment. Here, FIG. 5 illustrates a case where information of iFR is associated with and given on a contrast image. Specifically, in FIG. 5, blood vessels are colored at positions on the contrast image in accordance with absolute values of iFR. Plots at positions next to the blood vessels further indicate iFR drop rates at the positions. An iFR drop rate indicates how much an absolute value of iFR drops between adjacent positions of measurement. In FIG. 5, the plots are arranged in a direction orthogonal to a direction in which each of the blood vessels runs, and the higher the drop rate, the more the plots in number. For example, there are many plots at positions each where an absolute value of iFR changes significantly due to coarctation, for example (positions each where a change in color is significant in the figure).

When the identification function 110c identifies, as a target to be stored, a contrast image associated with such information of iFR, and the device operator has pressed down the storage button, the storage processing function 110d sets the state illustrated in FIG. 5 as a default, and causes the storage 111 to store the contrast image, data of iFR (values and positions of measurements), and display settings information (how the iFR is displayed). Display settings information includes information of coloring of values of iFR for display, color information corresponding to the values of iFR, information of how to display iFR drop rates with plots at positions next to blood vessels, and information of the iFR drop rates each corresponding to one plot, for example. Therefore, when the contrast image associated with the information of iFR illustrated in FIG. 5 is displayed again, the device operator can perform switching between a plot display of iFR drop rates and a colored display based on absolute values of iFR, and to correct a guideline for a pressure wire (including settings of a starting point and an ending point).

The embodiment has been described above with reference to the example of storing fluoroscopic images and captured images, for example. However, the embodiment is not limited to the above described example. For example, it is possible to store medical images received from an external apparatus. Although not illustrated in FIG. 2, it is possible to couple the X-ray diagnostic apparatus 10 with another modality or a peripheral device via a network to cause the examination room monitors 108a or the observation room monitors 108b to display medical images received from the modality or the peripheral device.

In such a case, the identification function 110c identifies, based on a last operation related to a medical image received from the external apparatus, the medical image as a target to be stored. As the storage button is pressed down, the storage processing function 110d causes the storage 111 to store the medical image. Here, the storage processing function 110d may capture a medical image displayed on each of the examination room monitors 108a or the observation room monitors 108b to cause the storage 111 to store the captured image, or may read, from the memory 107, data of a received medical image to cause the storage 111 to store the received medical image.

As described above, after the storage processing function 110d has caused the medical image to be stored, the output function 110b causes one of the examination room monitors 108a or the observation room monitors 108b to display the medical image that the storage 111 is caused to memorize. That is, a medical image stored during a medical operation is in many cases required to be seen during the medical operation, the output function 110b causes one of the examination room monitors 108a or the observation room monitors 108b to display the stored medical image.

Here, the output function 110b causes a medical image that is to be displayed, and that the storage 111 is caused to memorize, at a display position that is set per a kind of the identified medical image, a display position for a non-display state, or a display position at which the identified medical image has been displayed. For example, to cause one of the examination room monitors 108a or the observation room monitors 108b to display a stored medical image, the output function 110b causes a monitor determined beforehand to display a fluoroscopic image, a captured image, or a medical image received from an external apparatus. For example, the output function 110b causes a monitor that displays no image at this time to display a medical image that the storage 111 is caused to memorize. For example, the output function 110b causes the monitor that has displayed the medical image that the storage 111 is caused to memorize to continuously display the medical image.

Here, the output function 110b determines whether to display a medical image that the storage 111 is caused to memorize in accordance with a kind of the identified medical image. That is, if an image of a certain type is stored, the output function 110b can perform even such a control that the stored medical image is not displayed. For example, when a medical image received from an external apparatus is to be stored in the storage 111, the medical image is already displayed on one of the examination room monitors 108a or the observation room monitors 108b, and the output function 110b does not set the medical image as a target to be displayed.

The embodiment has been described above with reference to the case where the imaging portion has a single plane. However, the embodiment is not limited to the case. The imaging portion may have a biplane. That is, even when the imaging portion includes a first imaging system (e.g., the L side) and a second imaging system (e.g., the F side) each including the X-ray tube 102 and the X-ray detector 106, and the examination room monitors 108a and the observation room monitors 108b are each configured to display a plurality of medical images including X-ray images captured by the first imaging system and a plurality of medical images including X-ray images captured by the second imaging system, the X-ray diagnostic apparatus 10 can similarly perform storage processing, as described above.

In such a case, the examination room input interfaces 109a and the observation room input interface 109b each accept an operation instructing storage of one of the medical images related to the first imaging system and one of the medical images related to the second imaging system, which are displayed on the examination room monitors 108a and the observation room monitors 108b. That is, the examination room input interfaces 109a and the observation room input interface 109b each collectively or separately accept an operation instructing storage of one of the medical images related to the first imaging system and an operation instructing storage of one of the medical images related to the second imaging system. For example, the examination room input interfaces 109a and the observation room input interface 109b each accept, upon pressing down of the storage button, storage of a medical image related to the L side and storage of a medical image related to the F side.

For example, when a last operation involves an operation related to both a medical image related to the L side and a medical image related to the F side, the examination room input interfaces 109a and the observation room input interface 109b each accept pressing down of the storage button as storage of the medical image related to the L side and storage of the medical image related to the F side. For example, when a last operation involves an operation related to either a medical image related to the L side or a medical image related to the F side, the examination room input interfaces 109a and the observation room input interface 109b each accept pressing down of the storage button as storage of the medical image related to the last operation. The examination room input interfaces 109a and the observation room input interface 109b may always each accept pressing down of the storage button as storage of a medical image related to the L side and storage of a medical image related to the F side.

The identification function 110c identifies, for medical images related to the first imaging system and medical images related to the second imaging system, each medical image associated with a last-executed, targeted operation. The storage processing function 110d causes, upon the acceptance of an operation that is performed through the storage button, and that instructs storage of a medical image, the storage 111 to memorize each of the identified medical images.

Figure 6:
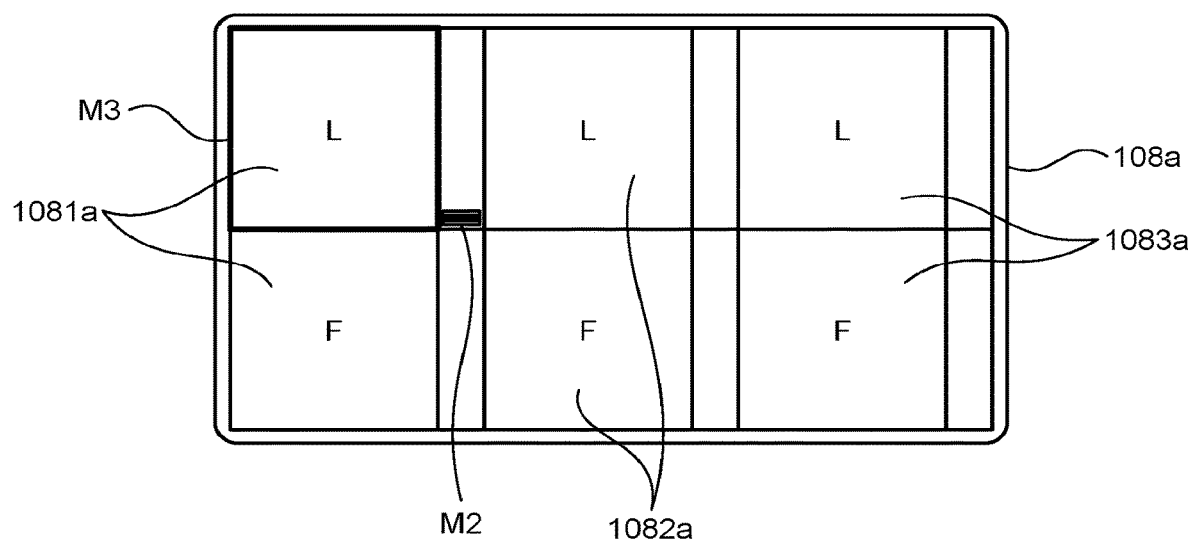
FIG. 6 is a view of example processing to be performed by the output function according to the first embodiment.

FIG. 6 is a view of example processing to be performed by the output function according to the first embodiment. Here, FIG. 6 illustrates an example case where one of the examination room monitors 108a is focused on. FIG. 6 illustrates the case where, as the examination room monitor 108a, the L side and the F side of the biplane each include the live monitor 1081a, the reference monitor 1082a and the additional monitor 1083a.

For example, when the device operator operates the fluoroscopy switch on the L side, collection of a fluoroscopic image starts, and the identification function 110c identifies the fluoroscopic image as a target image to be stored, the output function 110b causes, as illustrated in FIG. 6, the live monitor 1081a that displays the fluoroscopic image to display the marker M3. After that, when the device operator presses down the storage button, the storage processing function 110d causes the storage 111 to store the fluoroscopic image displayed when the storage button is pressed down, among fluoroscopic images that are each displayed on the live monitor 1081a on the L side.

The embodiment has been described above with reference to the case where the medical operator executes a device operation during a medical operation in the examination room R1. However, the embodiment is not limited to the case. Device operations may be executed in both of the examination room R1 and the observation room R2. That is, even when one of the storage buttons on the examination room input interfaces 109a and the observation room input interface 109b is pressed down, the X-ray diagnostic apparatus 10 can similarly perform storage processing, as described above.

In such a case, the identification function 110c identifies a medical image associated with a last-executed, targeted operation performed in the examination room R1 and a medical image associated with a last-executed, targeted operation performed in the observation room R2, respectively. That is, the identification function 110c identifies a medical image related to a last operation performed in the examination room R1 and a medical image related to a last operation performed in the observation room R2, respectively. For example, when the medical doctor A measures a distance on a medical image displayed on one of the reference monitors 1082a in the observation room R2, and the medical doctor B depresses the fluoroscopy switch in the examination room R1 to start manipulation with a fluoroscopic image displayed on the live monitor 1081a, the identification function 110c identifies, as a target to be stored, the medical image on which a distance is measured in the observation room R2, and identifies, in the examination room R1, the fluoroscopic image as a target to be stored.

The storage processing function 110d causes the storage 111 to store the identified medical image in response to an operation accepted by the storage button in the examination room R1, and causes the storage 111 to store the identified medical image in response to an operation accepted by the storage button in the observation room R2. For example, the storage processing function 110d causes, when the storage button is pressed down in the examination room R1, the storage 111 to store a fluoroscopic image displayed when the storage button is pressed down. The storage processing function 110d causes, when the storage button is pressed down in the observation room R2, the storage 111 to store a medical image that has been used to measure a distance when the storage button is pressed down.

Figure 7:
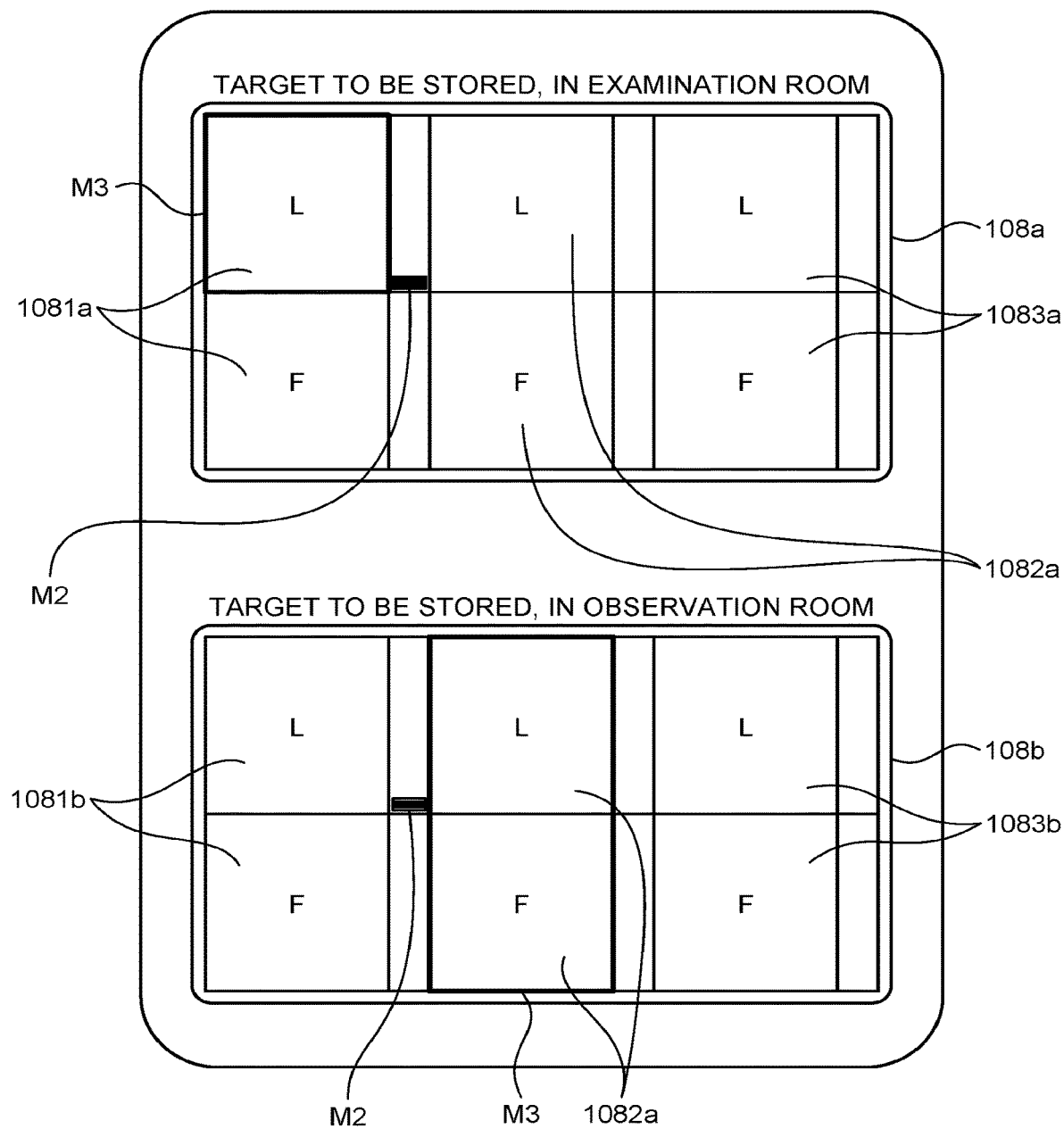
FIG. 7 is a view of example processing to be performed by the output function according to the first embodiment.

Here, when device operations are executed in the examination room R1 and the observation room R2, respectively, the output function 110b causes the examination room monitors 108a and the observation room monitors 108b to each display the marker used to recognize a medical image identified through a last operation. FIG. 7 is a view of example processing to be performed by the output function according to the first embodiment. Here, FIG. 7 vertically illustrates the examination room monitor 108a and the observation room monitor 108b, respectively. FIG. 7 illustrates the case where, as a monitor in each room, the L side and the F side of a biplane each include the live monitor 1081a, the reference monitor 1082a, and the additional monitor 1083a.

For example, when the medical doctor A measures a distance on medical images displayed on the reference monitors 1082a in the observation room R2, the output function 110b causes the reference monitors 1082a in the observation room monitor 108b to display the marker M3, as illustrated as a target to be stored, in the observation room in FIG. 7. For example, when the medical doctor B depresses the fluoroscopy switch in the examination room R1 to cause one of the live monitors 1081a to display a fluoroscopic image, the output function 110b causes the one of the live monitors 1081a in the examination room monitor 108a to display the marker M3, as illustrated as a target to be stored, in the examination room in FIG. 7.

The example has been described above with reference to the case where the device operator in the examination room R1 executes a storage operation, and the device operator in the observation room R2 executes a storage operation, respectively. However, either one of the device operators may execute a storage operation. In such a case, the identification function 110c identifies, as a target to be stored, a medical image having undergone a last operation, among operations performed by the device operator in the examination room R1 and operations performed by the device operator in the observation room R2, for example.

Here, to identify a target to be stored through one of operations performed by the device operator in the examination room R1 and operations performed by the device operator in the observation room R2, the priority may be set. For example, the identification function 110c preferentially identifies a medical image associated with a last-executed, targeted operation in the examination room R1. The storage processing function 110d causes, when the storage button on one of the examination room input interfaces 109a is pressed down, the storage 111 to memorize the identified medical image. For example, in the examination room R1, an image (e.g., a fluoroscopic image) necessary for manipulation is observed. Therefore, preferentially determining, as a last operation, an operation performed in the examination room R1 makes it possible to preferentially store an image necessary for manipulation.

As described above, the observation room input interface 109b according to the present embodiment is disposed with the active marker switching button used to move the position of the active marker, making it possible to move the position of the active marker M2 upon the acceptance of pressing down of the active marker switching button. Here, when the active marker switching button on the observation room input interface 109b is pressed down, the position of the active marker M2 moves, and a last operation in the observation room R2 only transitions.

That is, when the pressing down of the active marker switching button is regarded as a last operation to identify a target medical image to be stored, and the active marker switching button on the observation room input interface 109b is pressed down, the identification function 110c does not update the last operation identified in the examination room R1, but updates the last operation identified in the observation room R2 only. Such a case will be described below with reference to an example where it is identified, as a target to be stored, a medical image having undergone a last operation, among operations performed by the device operator in the examination room R1 and operations performed by the device operator in the observation room R2. In such a situation, when an operation performed by the device operator in the examination room R1 is identified as a last operation, and, after that, the active marker switching button on the observation room input interface 109b is pressed down, the identification function 110c keeps the last operation performed in the examination room R1, and determines the pressing down of the active marker switching button on the observation room input interface 109b as a last operation in the observation room R2. That is, the identification function 110c switches processing to identify a medical image based on a last operation performed by the device operator in the examination room R1 and a medical image based on a last operation performed by the device operator in the observation room R2, respectively.

Figure 8:
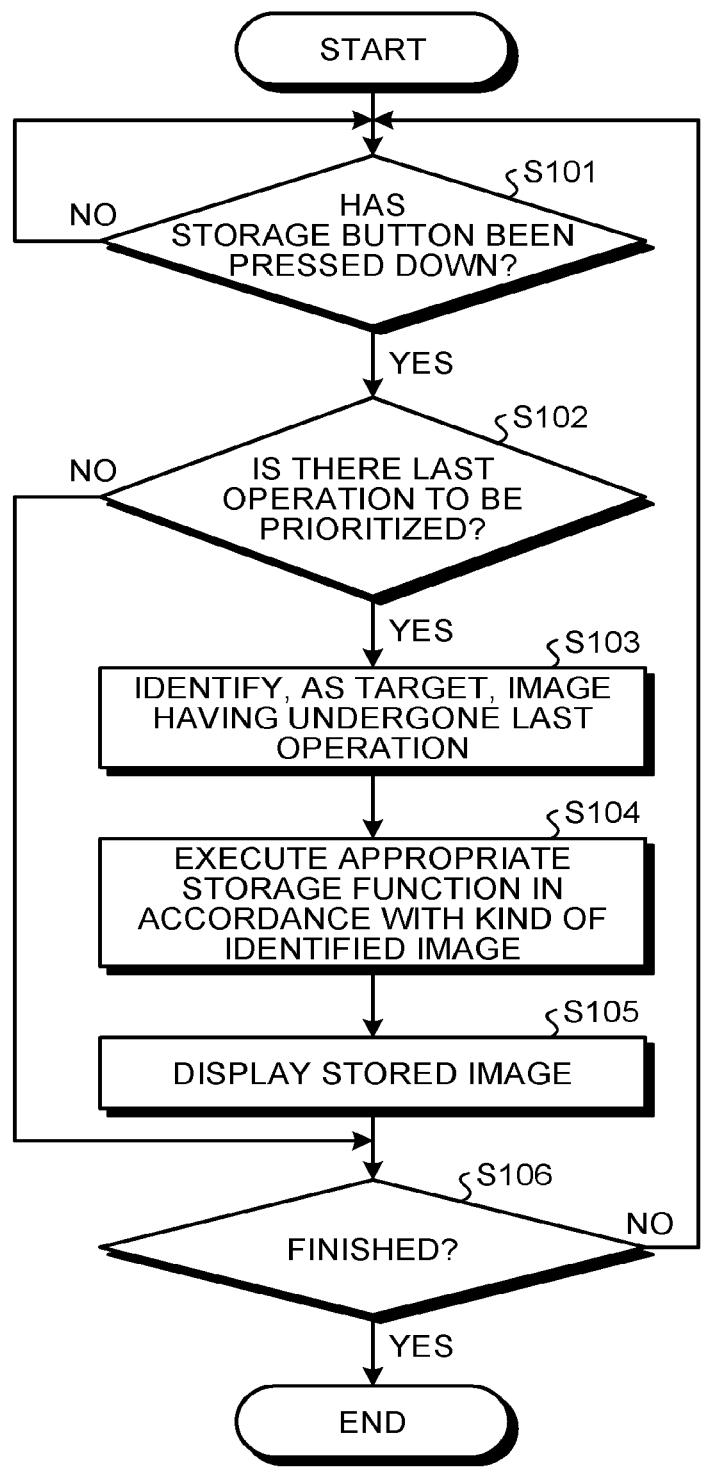
FIG. 8 is a flowchart of a processing flow to be performed by the X-ray diagnostic apparatus according to the first embodiment.

Next, an example processing flow to be performed by the X-ray diagnostic device 10 will be described with reference to FIG. 8. FIG. 8 is a flowchart of a processing flow to be performed by the X-ray diagnostic device 10 according to the first embodiment. Here, FIG. 8 illustrates the case where a last operation has been set with the priority. Steps S101 to S103 in FIG. 8 are steps achieved when the processing circuitry 110 reads and executes a computer program corresponding to the identification function 110c. Step S104 is a step achieved when the processing circuitry 110 reads and executes a computer program corresponding to the storage processing function 110d. Step S105 is a step achieved when the processing circuitry 110 reads and executes a computer program corresponding to the output function 110b. Step S106 is a step achieved when the processing circuitry 110 reads and executes a computer program corresponding to the control function 110a.

In the X-ray diagnostic apparatus 10 according to the first embodiment, the processing circuitry 110 determines whether one of the storage buttons is pressed down (step S101). Here, when one of the storage buttons is pressed down (Yes at step S101), the processing circuitry 110 determines whether there is a last operation to be prioritized (step S102). Until one of the storage buttons is pressed down, the processing circuitry 110 continues the determination in step S101 (No at step S101).

Here, when there is a last operation to be prioritized (Yes at step S102), the processing circuitry 110 identifies, as a target, an image having undergone a last operation (step S103), and executes an appropriate storage function in accordance with a kind of the identified image (step S104).

After that, the processing circuitry 110 causes each of the examination room monitors 108a and the observation room monitors 108b to display the stored image (step S105), and determines whether the processing flow has been finished (step S106). Here, when the processing flow has been finished (Yes at step S106), the processing circuitry 110 ends the processing flow. On the other hand, if the processing flow has not yet been finished (No at step S106), the processing circuitry 110 causes the processing flow to return to step S101 to continuously determine whether one of the storage buttons is pressed down. When there is no last operation to be prioritized at step S102 (No at step S102), the processing circuitry 110 executes a determination at step S106.

As described above, according to the first embodiment, the storage 111 is configured to memorize medical images. The imaging portion includes the X-ray tube 102 configured to emit X-rays toward a subject and the X-ray detector 106 configured to detect X-rays emitted from the X-ray tube 102. The examination room monitors 108a and the observation room monitors 108b are each configured to display a plurality of medical images including X-ray images captured by the imaging portion. The examination room input interfaces 109a and the observation room input interface 109b are each configured to accept an operation instructing storage of one of medical images displayed on the examination room monitors 108a and the observation room monitors 108b. The identification function 110c identifies a medical image associated with a last-executed, targeted operation, among targeted operations related to any of a plurality of medical images displayed on the examination room monitors 108a and the observation room monitors 108b. The storage processing function 110d causes, when one of the examination room input interfaces 109a and the observation room input interface 109b accepts an operation instructing storage of a medical image displayed on one of the examination room monitors 108a and the observation room monitors 108b, the storage 111 to memorize the identified medical image. Therefore, the X-ray diagnostic apparatus 10 according to the first embodiment makes it possible to store a desired medical image when one of the storage buttons is solely operated, achieving improved operability.

According to the first embodiment, the storage processing function 110d changes a type of a storage function in accordance with a kind of an identified medical image. Therefore, the X-ray diagnostic apparatus 10 according to the first embodiment makes it possible to store an image with a type appropriate for the image.

According to the first embodiment, the storage processing function 110d changes the type of the storage function to be associated with an operation to be accepted by each of the examination room input interfaces 109a and the observation room input interface 109b, between a case where an identified medical image is a fluoroscopic image and a case where an identified medical image is a captured image. Therefore, the X-ray diagnostic apparatus 10 according to the first embodiment makes it possible to appropriately store a fluoroscopic image and a captured image, respectively.

According to the first embodiment, the identification function 110c identifies a medical image associated with a targeted operation including at least one operation among operations related to generation, editing, and display of a medical image to be displayed on each of the examination room monitors 108a and the observation room monitors 108b. Therefore, the X-ray diagnostic apparatus 10 according to the first embodiment makes it possible to avoid an operation irrelevant to storage of an image from being determined as a last operation.

According to the first embodiment, the identification function 110c identifies a medical image associated with a last-executed, targeted operation, on the basis of priority set in accordance with a kind of a medical image. Therefore, the X-ray diagnostic apparatus 10 according to the first embodiment makes it possible to preferentially store an image in accordance with a kind of the image.

According to the first embodiment, the imaging portion includes the first imaging system and the second imaging system each including the X-ray tube 102 and the X-ray detector 106. The examination room monitors 108a and the observation room monitors 108b are each configured to display a plurality of medical images including X-ray images captured by the first imaging system and a plurality of medical images including X-ray images captured by the second imaging system, respectively. The examination room input interfaces 109a and the observation room input interface 109b each accept an operation instructing storage of one of medical images related to the first imaging system and one of medical images related to the second imaging system, which are displayed on the examination room monitors 108a and the observation room monitors 108b. The identification function 110c identifies, for the medical images related to the first imaging system and the medical images related to the second imaging system, each medical image associated with a last-executed, targeted operation. The storage processing function 110d causes, when one of the examination room input interface 109a and the observation room input interface 109b accepts an operation instructing storage of a medical image displayed on one of the examination room monitors 108a and the observation room monitors 108b, the storage 111 to memorize the identified medical image. Therefore, the X-ray diagnostic apparatus 10 according to the first embodiment makes it possible to store medical images displayed on the L side and the F side, respectively, of the biplane.

According to the first embodiment, the examination room input interfaces 109a and the observation room input interface 109b each collectively or separately accept an operation instructing storage of one of the medical images related to the first imaging system and an operation instructing storage of one of the medical images related to the second imaging system. Therefore, the X-ray diagnostic apparatus 10 according to the first embodiment makes it possible to appropriately store medical images captured in various kinds of situations.

According to the first embodiment, medical images include medical images accepted from the outside of the X-ray diagnostic apparatus 10. Therefore, the X-ray diagnostic apparatus 10 according to the first embodiment makes it possible to execute storage processing for all medical images displayed on the examination room monitors 108a and the observation room monitors 108b.

According to the first embodiment, the storage processing function 110d causes the storage 111 to memorize supplementary information given on an identified medical image, in such a manner that the supplementary information is associated with the identified medical image. Therefore, the X-ray diagnostic apparatus 10 according to the first embodiment makes it possible to display a medical image and supplementary information, respectively.

According to the first embodiment, the storage processing function 110d causes the storage 111 to memorize supplementary information, in such a manner that the supplementary information is associated with a given position on a medical image. Therefore, the X-ray diagnostic apparatus 10 according to the first embodiment makes it possible to display a medical image together with given supplementary information in one of various kinds of forms.

According to the first embodiment, the examination room monitors 108a and the observation room monitors 108b are respectively disposed in the examination room in which the imaging portion captures images and the observation room in which the X-ray diagnostic apparatus 10 is operated. The examination room input interfaces 109a and the observation room input interface 109b are respectively disposed in the examination room in which the imaging portion captures images and the observation room in which the X-ray diagnostic apparatus is operated. The identification function 110c identifies a medical image associated with a last-executed, targeted operation performed in the examination room and a medical image associated with a last-executed, targeted operation performed in the observation room, respectively. The storage processing function 110d causes the storage 111 to memorize the identified medical image, in response to an operation accepted by each of the examination room input interfaces 109a in the examination room and the identified medical image, in response to an operation accepted by the observation room input interface 109b in the observation room, respectively. Therefore, the X-ray diagnostic apparatus 10 according to the first embodiment makes it possible to achieve improved operability regarding storage processing for medical images captured in the examination room R1 and the observation room R2, respectively.

According to the first embodiment, the identification function 110c preferentially identifies a medical image associated with a last-executed, targeted operation in the examination room. Therefore, the X-ray diagnostic apparatus 10 according to the first embodiment makes it possible to preferentially execute storage processing in the examination room in which manipulation takes place.

According to the first embodiment, the output function 110b causes the examination room monitors 108a and the observation room monitors 108b to each display a medical image that the storage 111 is caused to memorize. Therefore, the X-ray diagnostic apparatus 10 according to the first embodiment makes it possible to promptly display a medical image desired to be seen during manipulation.

According to the first embodiment, the output function 110b causes a medical image that is to be displayed, and that the storage 111 is caused to memorize, at a display position that is set per a kind of the identified medical image, a display position for a non-display state, or a display position at which the identified medical image has been displayed. Therefore, the X-ray diagnostic apparatus 10 according to the first embodiment makes it possible to display a medical image at an appropriate position in accordance with a situation.

According to the first embodiment, the output function 110b determines whether to display a medical image that the storage 111 is caused to memorize in accordance with a kind of the identified medical image. Therefore, the X-ray diagnostic apparatus 10 according to the first embodiment makes it possible to avoid an unnecessary medical image from being displayed.

According to the first embodiment, the output function 110b causes the examination room monitors 108a and the observation room monitors 108b to display information allowing an identified medical image to be recognized. Therefore, the X-ray diagnostic apparatus 10 according to the first embodiment allows a device operator to know at one view a target medical image to be stored.

According to the first embodiment, the special switches are respectively linked to a plurality of display regions (e.g., the live monitor, the reference monitor, and the additional monitor) included in each of the examination room monitors 108a and the observation room monitors 108b to accept an operation for a medical image displayed on each of the display regions that are linked to the operation switches. The control function 110a sets a target to be operated without using the special buttons. The examination room monitors 108a and the observation room monitors 108b each display the active marker used to recognize a target to be operated without using the special buttons. The identification function 110c causes, in accordance with a targeted operation by using one of the special buttons, medical images to transition, one of which is to be identified. Meanwhile, the control function 110a does not change the target to be set, depending on a targeted operation by using one of the special buttons. Therefore, the X-ray diagnostic apparatus 10 according to the first embodiment makes it possible to keep the convenience of the special buttons, achieving improved operability.

SECOND EMBODIMENT

Figure 9:
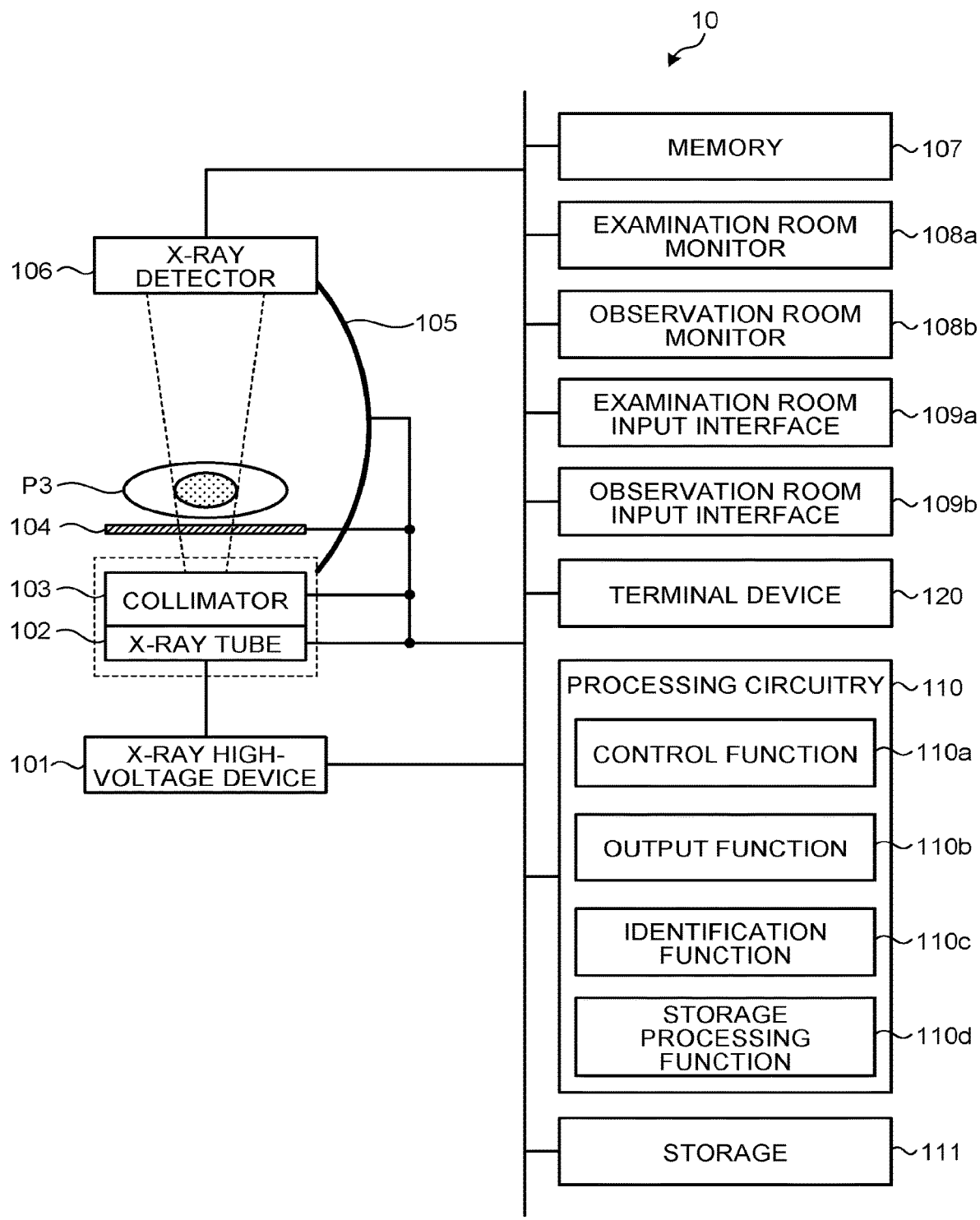
FIG. 9 is a block diagram of a configuration example of an X-ray diagnostic apparatus according to a second embodiment.

In the first embodiment, the case has been described where a plurality of device operators in the examination room R1 and the observation room R2 respectively perform device operations. In the second embodiment, such a case will be described that a plurality of device operators in the examination room R1 respectively perform device operations. FIG. 9 is a block diagram of a configuration example of the X-ray diagnostic apparatus 10 according to the second embodiment. The X-ray diagnostic apparatus 10 according to the second embodiment includes a terminal apparatus 120, and the output function 110b and the identification function 110c execute different processing, compared with the first embodiment. The differences will be focused on and described below.

With the X-ray diagnostic apparatus 10 according to the second embodiment, the terminal apparatus 120 is provided in the examination room R1. That is, in the examination room R1, the terminal apparatus 120 is provided to serve as another examination room input interface 109a, in addition to the examination room input interfaces 109a including the table-side console, for example.

The terminal apparatus 120 is, for example, a remote console that allows the X-ray diagnostic apparatus 10 to be remote-operated, or a tablet terminal that is coupled in an accessible manner to the X-ray diagnostic apparatus 10 via radio communications, and that includes an application to be executed to remote-operate the input interfaces of the X-ray diagnostic apparatus 10. For example, the tablet terminal as described above accepts operations. As the X-ray diagnostic apparatus receives the operations via radio communications, the tablet terminal remotely operates the input interfaces including the mouse and the keyboard, for example. In an example case, one of the device operators in the examination room R1 uses, as a touch pad, a touch panel of the tablet terminal to operate a pointer displayed on each of the examination room monitors 108a to execute an operation on a GUI displayed on an examination room display. Here, displays on the touch panel of the tablet terminal and the each of the examination room monitors 108a can be synchronized.

The identification function 110c according to the second embodiment identifies medical images respectively associated with last-executed, targeted operations by the device operators operating the examination room input interfaces 109a and the terminal apparatus 120 in the examination room. That is, the identification function 110c identifies a medical image related to a last operation performed on one of the examination room input interfaces 109a and a medical image related to a last operation performed on the terminal apparatus 120, respectively.

The storage processing function 110d according to the second embodiment causes the storage 111 to memorize identified medical images, respectively, in response to operations accepted by the examination room input interfaces 109a and the terminal apparatus 120. For example, the storage processing function 110d causes the storage 111 to memorize fluoroscopic images in response to operations performed on the examination room input interfaces 109a, and causes the storage 111 to memorize captured images in response to operations performed on the terminal apparatus 120.

Here, in the second embodiment, to store medical images, it is possible to accept operations performed on the examination room input interfaces 109a and operations performed on the terminal apparatus 120. That is, such a configuration is possible that the device operators operate the examination room input interfaces 109a and the terminal apparatus 120 to cause medical images to be stored.

In such a case, for example, the identification function 110c identifies, as a last operation, either one of an operation performed on one of the examination room input interfaces 109a and an operation performed on the terminal apparatus 120, whichever is performed last. Here, to identify, as a last operation, either one of an operation performed on one of the examination room input interfaces 109a and an operation performed on the terminal apparatus 120, whichever is performed last, the operations may conflict with each other, possibly quickly switching target medical images to be stored.

The identification function 110c can thus determine a last operation on the basis of priority set for each of kinds of operations and the input interfaces. For example, the identification function 110c preferentially selects an operation related to collection of an X-ray image, as a last-executed, targeted operation. For example, the medical operator focuses on each of the live monitors 1081a during fluoroscopy. The identification function 110c can thus determine a fluoroscopic image as a target to be stored during fluoroscopy only. After the fluoroscopy, the identification function 110c can change back the target to be stored to a medical image which has been operated immediately previously.

This is a necessary mechanism in such a scene that a plurality of device operators are operating devices simultaneously in an examination room. For example, the medical doctor A is inserting a catheter during fluoroscopy, and the medical doctor B edits an image displayed on each of the reference monitors 1082a. If collection of an X-ray image is not prioritized, even when the medical doctor A wants to store a still image during fluoroscopy, under such a situation that the medical doctor B is operating an image displayed on each of the reference monitors 1082a, a target to be stored is set to a medical image displayed on each of the reference monitors 1082a. It is therefore impossible to store a fluoroscopic image displayed on each of the live monitors 1081a. When an X-ray image is being collected, the identification function 110c then preferentially identifies the X-ray image being collected as a target to be stored.

For example, the identification function 110c identifies a medical image associated with a last-executed, targeted operation, on the basis of priority set for each of the examination room input interfaces 109a and the terminal apparatus 120 provided in the examination room. In an example case, an order of the priority is set as "table-side console>terminal apparatus".

In such a case, the identification function 110c identifies, as a target to be stored, a medical image related to an operation performed on the table-side console. Here, for example, the identification function 110c may keep prioritizing the table-side console until a certain time has elapsed from when an operation performed on the table-side console has been accepted.

At this time, when the terminal apparatus 120 is a tablet terminal, a storage switch on the tablet terminal may be changed to a switch for a storage function limited to the tablet terminal, instead of a standard storage switch for a whole system. That is, when an operation to be performed on the table-side console is prioritized, the tablet terminal allows storage of a medical image limited on the tablet terminal. In that case, for example, each of the device operators can operate the tablet terminal to display again a medical image to execute a storage operation for the image. In this case, the GUI of the storage button may not be changed. The function of the storage button may only be switched. The design (icon) of the GUI may otherwise be changed.

Here, when a plurality of tablet terminals are coupled, the tablet terminals are set with the priority. For example, the priority is set to the operators operating the tablet terminals. In an example case, an order of the priority is set as "doctor's tablet terminal>staff's tablet terminal". That is, the identification function 110c preferentially identifies a target medical image to be stored in the order of table-side console, doctor's tablet terminal, and staff's tablet terminal.

The identification function 110c can determine information related to each of the device operators of the tablet terminals, on the basis of entered identification information of each of the device operators of the tablet terminals. Even if identification information of the device operators of the tablet terminals has not yet been entered, the identification function 110c can determine the device operators, on the basis of positions at which the tablet terminals are provided.

In an example case, the identification function 110c determines the priority such that the closer the distance from the tabletop, the higher the priority. Here, the positions of the tablet terminals may be acquired from position sensors, when the position sensors are respectively attached to the tablet terminals, for example. Identifiers may be respectively disposed at the positions (e.g., the table side and the remote console) at which the tablet terminals are provided to acquire the positions of the tablet terminals from the identifiers.

As described above, the second embodiment has been described with reference to the case where the device operators in the examination room R1 respectively perform device operations. Here, the output function 110b can cause the examination room monitors 108a, for example, to each display a marker used to recognize a medical image related to a last operation, similarly to the first embodiment.

When the terminal apparatus 120 is a tablet terminal, the output function 110b can cause the examination room monitors 108a and the tablet terminal to each display the marker. Here, the output function 110b can cause to display a marker and information indicating that displays on the examination room monitors 108a and the tablet terminal are synchronized or information indicating that the displays are not synchronized.

Figure 11:
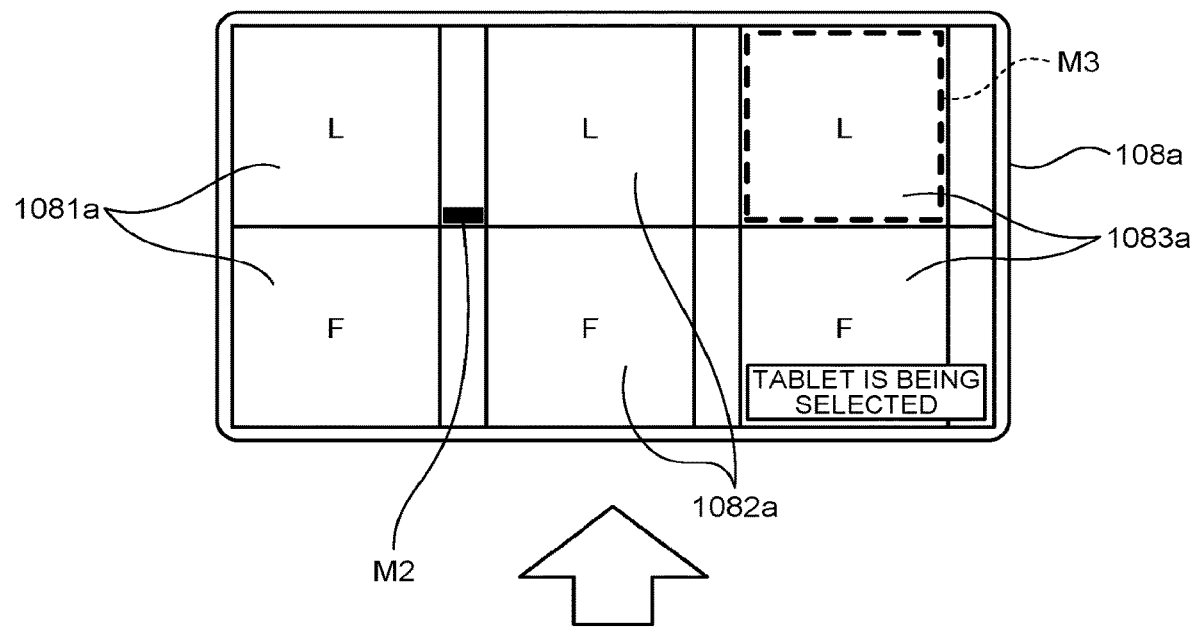
FIG. 11 is a view of example processing to be performed by the output function according to the second embodiment.

FIGS. 10 and 11 are views of example processing to be performed by the output function according to the second embodiment. FIG. 10 illustrates a case where displays on the examination room monitors 108a and the tablet terminal are synchronized. FIG. 11 illustrates a case where displays on the examination room monitors 108a and the tablet terminal are not synchronized.

For example, when an identical application is launched on the tablet terminal, and displayed contents are synchronized, the output function 110b causes the marker M3 and a marker M4, which each surround with a solid line a medical image identified by the identification function 110c, to be respectively displayed on the examination room monitors 108a and the tablet terminal, as illustrated in FIG. 10. Here, when the device operator of the tablet terminal edits the image displayed on the tablet terminal, the image displayed on the corresponding one of the additional monitors in each of the examination room monitors 108a is also updated to the edited image.

For example, if the displayed contents are not synchronized, the output function 110b causes to display one of the markers with a dotted line, and causes to display information indicating that which of the devices is active, as illustrated in FIG. 11. In FIG. 11, the tablet terminal is active. The output function 110b therefore causes the tablet terminal to display the marker M4 with the solid line, causes each of the examination room monitors 108a to display the marker M3 with the dotted line, and causes to display a message "Tablet is being selected." indicating that the tablet terminal is active. Here, when the image is closed on the tablet terminal, for example, the examination room monitors 108a become active. The output function 110b then causes the dotted line indicating the marker M3 to change to the solid line.

As described above, the priority of an operation related to collection of an X-ray image is higher, and, for example, when the device operator depresses the fluoroscopy switch while the tablet terminal is active, the examination room monitors 108a become active. The output function 110b then causes the dotted line indicating the marker M3 to change to the solid line. As the fluoroscopy ends, the tablet terminal becomes active again.

Figure 12:
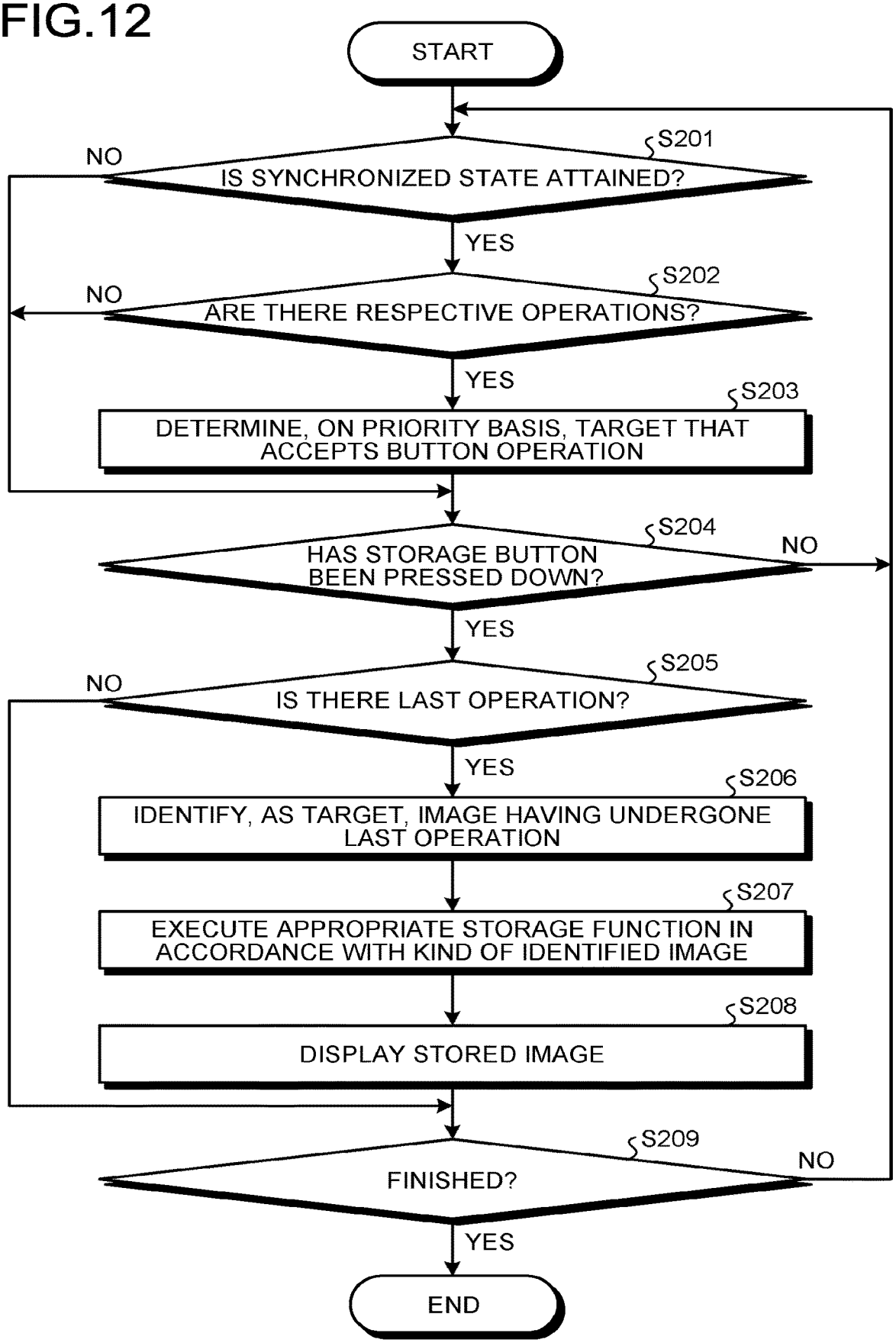
FIG. 12 is a flowchart of a processing flow to be performed by the X-ray diagnostic apparatus according to the second embodiment.

Next, an example processing flow to be performed by the X-ray diagnostic apparatus 10 according to the second embodiment will be described with reference to FIG. 12. FIG. 12 is a flowchart of a processing flow to be performed by the X-ray diagnostic apparatus 10 according to the second embodiment. Steps S201 to S206 in FIG. 12 are steps achieved when the processing circuitry 110 reads and executes a computer program corresponding to the identification function 110c. Step S207 is a step achieved when the processing circuitry 110 reads and executes a computer program corresponding to the storage processing function 110d. Step S208 is a step achieved when the processing circuitry 110 reads and executes a computer program corresponding to the output function 110b. Step S209 is a step achieved when the processing circuitry 110 reads and executes a computer program corresponding to the control function 110a.

In the X-ray diagnostic apparatus 10 according to the second embodiment, the processing circuitry 110 determines whether a synchronized state is attained (step S201). Here, if no synchronized state is attained (No at step S201), the processing circuitry 110 causes the processing flow to proceed to step S204. On the other hand, when a synchronized state is attained (Yes at step S201), the processing circuitry 110 determines whether the examination room input interfaces 109a and the terminal apparatus 120 are each operated (step S202).

Here, if the devices are not each operated (No at step S202), the processing circuitry 110 causes the processing flow to proceed to step S204. On the other hand, when the devices are each operated (Yes at step S202), the processing circuitry 110 determines, on a priority basis, a target that accepts a button operation (step S203).

After that, the processing circuitry 110 determines whether one of the storage buttons is pressed down (step S204). Here, if no storage button is pressed down (No at step S204), the processing circuitry 110 causes the processing flow to return to step S201 to execute a determination. On the other hand, when one of the storage buttons is pressed down (Yes at step S204), the processing circuitry 110 determines whether there is a last operation (step S205). Here, when there is a last operation (Yes at step S205), the processing circuitry 110 identifies, as a target, an image having undergone a last operation (step S206), and executes an appropriate storage function in accordance with a kind of the identified image (step S207).

After that, the processing circuitry 110 causes the examination room monitors 108a to display the stored image (step S208), and determines whether the processing flow has been finished (step S209). Here, when the processing flow has been finished (Yes at step S209), the processing circuitry 110 ends the processing flow. On the other hand, if the processing has not yet been finished (No at step S209), the processing circuitry 110 causes the processing flow to return to step S101 to execute a determination. At step S205, if there is no last operation (No at step S205), the processing circuitry 110 executes a determination at step S209.

As described above, according to the second embodiment, the examination room input interfaces 109a and the terminal apparatus 120 are provided in the examination room in which the imaging portion captures images. The identification function 110c identifies medical images respectively associated with last-executed, targeted operations by the device operators operating the examination room input interfaces 109a and the terminal apparatus 120 in the examination room R1. The storage processing function 110d causes the storage 111 to memorize identified medical images, respectively, in response to operations accepted by the examination room input interfaces 109a and the terminal apparatus 120 in the examination room R1. Therefore, the X-ray diagnostic apparatus 10 according to the second embodiment makes it possible to appropriately store medical images even when a plurality of device operators in an examination room perform device operations.

According to the second embodiment, the identification function 110c preferentially selects an operation related to collection of an X-ray image, as a last-executed, targeted operation. Therefore, the X-ray diagnostic apparatus 10 according to the second embodiment makes it possible to preferentially set an X-ray image to be collected as a target to be stored.

According to the second embodiment, at least one of the terminal apparatuses provided in the examination room is a tablet terminal configured to display each of a plurality of medical images. Therefore, the X-ray diagnostic apparatus 10 according to the second embodiment makes it possible to appropriately store medical images even in a system including a tablet terminal.

According to the second embodiment, the display portions on the examination room monitors 108a and the terminal apparatus 120 each display information indicating that displays on the examination room monitors 108a and the terminal apparatus 120 are synchronized or information indicating that the displays are not synchronized. Therefore, the X-ray diagnostic apparatus 10 according to the second embodiment allows a device operator to know at one view a state of synchronization.

According to the second embodiment, the identification function 110c identifies a medical image associated with a last-executed, targeted operation, on the basis of priority set for each of the examination room input interfaces 109a and the terminal apparatus 120 provided in the examination room R1. Therefore, the X-ray diagnostic apparatus 10 according to the second embodiment makes it possible to prevent a conflict from occurring.

According to the second embodiment, the priority is set higher as a distance from the tabletop on which a subject is at a recumbent position becomes closer. Therefore, the X-ray diagnostic apparatus 10 according to the second embodiment makes it possible to easily acquire the priority.

According to the second embodiment, the priority is set in accordance with the device operators. Therefore, the X-ray diagnostic apparatus 10 according to the second embodiment makes it possible to store a medical image appropriately on a priority basis.

OTHER EMBODIMENTS

The first and second embodiments have been described so far. However, other various kinds of embodiments than the first and second embodiments described above may be implemented.

The embodiments have been described above with reference to the cases where, in the examination room R1, the examination room input interfaces 109a each include the storage button used to store a medical image. However, the embodiments are not limited to the cases. The examination room input interfaces 109a may each include a plurality of such storage buttons as described above. The embodiments have been described with reference to the cases where, in the observation room R2, the observation room input interface 109b includes the storage button used to store a medical image. However, the embodiments are not limited to the cases. The observation room input interface 109b may include a plurality of such storage buttons as described above.

In the X-ray diagnostic apparatus 10 illustrated in each of FIGS. 1 and 9, the processing functions are each memorized in the storage 111 in the form of a computer program that a computer can execute. The processing circuitry 110 is a processor that reads and executes a computer program from the storage 111 to achieve a function corresponding to the computer program. In other words, the processing circuitry 110 that has read a computer program possesses a function corresponding to the read computer program. FIG. 1 has illustrated the case where the processing circuitry 110 solely achieves the processing functions of the control function 110a, the output function 110b, the identification function 110c, and the storage processing function 110d. However, the embodiments are not limited to the case. For example, the processing circuitry 110 may include a plurality of independent processors in a combined manner. The processors may respectively execute computer programs to achieve the processing functions. The processing functions that the processing circuitry 110 possesses may be achieved appropriately in an integrated manner into a single processing circuit or in a dispersed manner among a plurality of processing circuits.

The term "processor" described above means, for example, circuitry including a central processing unit (CPU), a graphics processing unit (GPU), an application specific integrated circuit (ASIC), and a programmable logic device (e.g., a simple programmable logic device (SPLD), a complex programmable logic device (CPLD), and a field programmable gate array (FPGA)). The processor reads and executes a computer program stored in the storage 111 to achieve a function.

With reference to FIGS. 1 and 9, it has been described that the storage 111 memorizes computer programs corresponding to the processing functions. However, such a configuration may be applied that a plurality of the storages 111 are disposed in a dispersed manner, and the processing circuitry 110 separately reads a corresponding computer program from the storages 111. Instead of storing computer programs in the storage 111, such a configuration may be applied that computer programs are directly incorporated in a circuit in a processor. In this case, the processor reads and executes the computer programs incorporated in the circuit to achieve the functions.

The above components of the devices according to the embodiments are functionally and schematically illustrated, and may not be necessarily physically configured as illustrated. That is, a specific, dispersed or integrated form of the devices is not limited to the forms illustrated in the embodiments. The devices may be wholly or partially and functionally or physically configured in a dispersed or integrated manner in terms of a desired unit in accordance with various kinds of loads and use situations, for example. Furthermore, the processing functions implemented in the devices may be wholly or partially achieved as desired through a CPU and a computer program analyzed and executed by the CPU, or achieved as wired logic hardware.

The above described control methods according to the embodiments can be achieved by causing a computer, such as a personal computer or a work station, to execute a control computer program prepared beforehand. The control computer program can be distributed via a network such as the Internet. The control computer program can be recorded in a computer readable, non-transitory recording medium such as a hard disk, a flexible disc (FD), a compact disc read only memory (CD-ROM), a magneto-optical disk (MO), or a digital versatile disc (DVD) to allow a computer to read and execute the control computer program from the recording medium.

According to at least one of the embodiments described above, it is possible to achieve improved operability.

With regard to the embodiments described above, notes will be disclosed below as aspects and selective features of the present invention.

Note 1

An X-ray diagnostic apparatus including:
  a storage configured to memorize medical images;
  an imaging equipment including an X-ray tube configured to emit X-rays toward a subject and a detector configured to detect X-rays emitted from the X-ray tube;
  a display configured to display a plurality of medical images including X-ray images captured by the imaging equipment;
  an input interface configured to accept an operation instructing storage of a medical image displayed on the display; and
  processing circuitry configured to identify a medical image associated with a last-executed, targeted operation, among targeted operations related to any of medical images displayed on the display, and, when the input interface has accepted an operation instructing storage of a medical image displayed on the display, to cause the storage to memorize the identified medical image.

Note 2

The processing circuitry may change a type of a storage function in accordance with a kind of the identified medical image.

Note 3

The processing circuitry may change the type of the storage function to be associated with an operation to be accepted by the input interface, between a case where the identified medical image is a fluoroscopic image and a case where the identified medical image is a captured image.

Note 4

The processing circuitry may identify a medical image associated with a targeted operation including at least one operation among operations related to generation, editing, and display of a medical image to be displayed on the display.

Note 5

The processing circuitry may identify a medical image associated with a last-executed, targeted operation, on the basis of priority set in accordance with a kind of the medical image.

Note 6

The imaging equipment may include a first imaging system and a second imaging system each including the X-ray tube and the detector,
  the display may be configured to display a plurality of medical images including X-ray images captured by the first imaging system and a plurality of medical images including X-ray images captured by the second imaging system, respectively,
  the input interface may accept an operation instructing storage of a medical image related to the first imaging system and a medical image related to the second imaging system displayed, respectively, on the display, and
  the processing circuitry may identify, for medical images related to the first imaging system and medical images related to the second imaging system, each medical image associated with a last-executed, targeted operation, and, when the input interface has accepted an operation instructing storage of a medical image displayed on the display portion, cause the storage to memorize the each identified medical image.

Note 7

The input interface may collectively or separately accept an operation instructing storage of a medical image related to the first imaging system and an operation instructing storage of a medical image related to the second imaging system.

Note 8

The medical images may include medical images accepted from the outside of the X-ray diagnostic apparatus.

Note 9

The processing circuitry may cause the storage to memorize supplementary information given on the identified medical image, in such a manner that the supplementary information is associated with the identified medical image.

Note 10

The processing circuitry may cause the storage to memorize the supplementary information, in such a manner that the supplementary information is associated with a given position on the medical image.

Note 11

The display may be disposed in each of an examination room in which the imaging equipment captures images and an observation room in which the X-ray diagnostic apparatus is operated,
  the input interface may be disposed in each of the examination room in which the imaging equipment captures images and the observation room in which the X-ray diagnostic apparatus is operated, and
  the processing circuitry may identify a medical image associated with a last-executed, targeted operation in the examination room and a medical image associated with a last-executed, targeted operation in the observation room, respectively, and cause the storage to memorize the identified medical image, in response to an operation accepted by the input interface in the examination room and the identified medical image, in response to an operation accepted by the input interface in the observation room, respectively.

Note 12

The processing circuitry may preferentially identify a medical image associated with a last-executed, targeted operation in the examination room.

Note 13

A plurality of the input interfaces may be disposed in the examination room in which the imaging equipment captures images, and
  the processing circuitry may identify a medical image associated with a last-executed, targeted operation by a device operator operating the input interfaces in the examination room, and cause the storage to memorize the identified medical image, in response to an operation accepted by each of the input interfaces in the examination room.

Note 14

The processing circuitry may preferentially select an operation related to collection of an X-ray image, as a last-executed, targeted operation.

Note 15

At least one of the input interfaces disposed in the examination room may represent a terminal apparatus configured to display each of the medical images.

Note 16

The display and a display of the terminal apparatus may each display information indicating that displays on the display and the terminal apparatus are synchronized or information indicating that the displays are not synchronized.

Note 17

The processing circuitry may identify a medical image associated with a last-executed, targeted operation, on the basis of priority set for each of a plurality of input interfaces disposed in the examination room.

Note 18

The priority may be set higher as a distance from the tabletop on which the subject is at a recumbent position to the input interface becomes closer.

Note 19

The priority may be set in accordance with each of operators operating the input interfaces.

Note 20

The processing circuitry may cause the display to display a medical image that the storage is caused to memorize.

Note 21

The processing circuitry may cause a medical image that is to be displayed, and that the storage is caused to memorize, at a display position that is set per a kind of the identified medical image, a display position for a non-display state, or a display position at which the identified medical image has been displayed.

Note 22

The processing circuitry may determine whether to display a medical image that the storage is caused to memorize, in accordance with a kind of the identified medical image.

Note 23

The processing circuitry may cause the display to display information allowing the identified medical image to be recognized.

Note 24

Operation switches respectively linked to a plurality of display regions included in the display, which are each configured to accept an operation for a medical image displayed on each of the display regions that are linked to the operation switches may be further included,
  the display portion may display information for identifying a target to be operated without using the operation switches, and
  the processing circuitry may set a target to be operated without using the operation switches, and cause, in accordance with a targeted operation by using one of the operation switches, medical images to transition, one of which is to be identified, and, meanwhile, may not change the target to be set, depending on a targeted operation by using one of the operation switches.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
a storage configured to memorize a plurality of medical images;
an imaging equipment including an X-ray tube configured to emit X-rays toward a subject and a detector configured to detect X-rays emitted from the X-ray tube;
a display configured to display a plurality of medical images including X-ray images captured by the imaging equipment;
an input interface configured to accept an operation instructing storage of one medical image of the plurality of medical images displayed on the display; and
processing circuitry configured to identify, when the input interface has accepted the operation instructing storage of the one medical image of the plurality of medical images displayed on the display, among the plurality of medical images, a medical image corresponding to an operation that was last-executed by an operator, among operations executed by the operator to generate a medical image to be displayed on the display and operations executed by the operator to display a medical image on the display, and configured to cause the storage to memorize the identified medical image without accepting an operation instructing storage of the identified medical image.

2. The X-ray diagnostic apparatus according to claim 1, wherein the processing circuitry is configured to change a type of a storage function in accordance with a kind of the identified medical image.

3. The X-ray diagnostic apparatus according to claim 1, wherein the operation last-executed by an operator includes at least one operation among operations related to generation, editing, and display of the one medical image of the plurality of medical images to be displayed on the display.

4. The X-ray diagnostic apparatus according to claim 1, wherein the processing circuitry is configured to identify one medical image of the plurality of medical images associated with a last-executed operation, based upon a priority set in accordance with a kind of the one medical image.

5. The X-ray diagnostic apparatus according to claim 1, wherein the medical images include medical images accepted from outside of the X-ray diagnostic apparatus.

6. The X-ray diagnostic apparatus according to claim 1, wherein the processing circuitry is configured to cause the storage to memorize supplementary information given on the identified medical image in such a manner that the supplementary information is associated with the identified medical image.

7. The X-ray diagnostic apparatus according to claim 1, wherein
the display is disposed in each of an examination room in which the imaging equipment captures images and an observation room in which the X-ray diagnostic apparatus is operated,
the input interface is disposed in each of the examination room in which the imaging equipment captures images and the observation room in which the X-ray diagnostic apparatus is operated, and
the processing circuitry is configured to identify a medical image of the plurality of medical images associated with a last-executed operation in the examination room and a medical image of the plurality of medical images associated with a last-executed operation in the observation room, respectively, and to cause the storage to memorize the identified medical image in response to an operation accepted by the input interface in the examination room and the identified medical image in response to an operation accepted by the input interface in the observation room, respectively.

8. The X-ray diagnostic apparatus according to claim 1, wherein
a plurality of the input interfaces are disposed in an examination room in which the imaging equipment captures images, and
the processing circuitry is configured to identify a medical image of the plurality of medical images associated with a last-executed operation by a device operator operating the plurality of the input interfaces in an examination room, and cause the storage to memorize the identified medical image, in response to the operation accepted by each of the input interfaces in the examination room.

9. The X-ray diagnostic apparatus according to claim 1, wherein the processing circuitry is configured to cause the display to display the identified medical image of the plurality of medical images that the storage is caused to memorize.

10. The X-ray diagnostic apparatus according to claim 1, wherein the processing circuitry is configured to cause the display to display information allowing the identified medical image to be recognized.

11. The X-ray diagnostic apparatus according to claim 1, further comprising operation switches respectively linked to a plurality of display regions included in the display, each of the operation switches being each configured to accept an operation for a medical image displayed on each of the display regions, wherein
the display displays information for identifying a target to be operated without using the operation switches, and
the processing circuitry sets a target to be operated without using the operation switches, causes, in accordance with a targeted operation by using one of the operation switches, medical images to transition, one of which is to be identified, and does not change the target to be set depending on a targeted operation by using one of the operation switches.

12. The X-ray diagnostic apparatus according to claim 1, further comprising a foot switch configured to accept instructions for acquiring a plurality of fluoroscopic images that are the plurality of images, wherein the processing circuitry is further configured to, while continuing to accept instructions for acquiring the plurality of fluoroscopic images from the operator, identify a fluoroscopic image of the plurality of fluoroscopic images as a target to be memorized even when an operation for another medical image is executed.

13. The X-ray diagnostic apparatus according to claim 2, wherein the processing circuitry is configured to change the type of the storage function to be associated with the operation to be accepted by the input interface between a case where the identified medical image is a fluoroscopic image and a case where the identified medical image is a captured image.

14. The X-ray diagnostic apparatus according to claim 6, wherein the processing circuitry is configured to cause the storage to memorize the supplementary information in such a manner that the supplementary information is associated with a given position on the medical image.

15. The X-ray diagnostic apparatus according to claim 7, wherein the processing circuitry is configured to preferentially identify the medical image of the plurality of medical images associated with a last-executed operation in the examination room.

16. The X-ray diagnostic apparatus according to claim 8, wherein the processing circuitry is configured to select an operation related to collection of an X-ray image, as a last-executed operation.

17. The X-ray diagnostic apparatus according to claim 8, wherein at least one of the input interfaces disposed in the examination room represents a terminal apparatus configured to display each of the plurality of medical images.

18. The X-ray diagnostic apparatus according to claim 9, wherein the processing circuitry is configured to cause the medical image of the plurality of medical images to be displayed at a display position that is set per a kind of the identified medical image, a display position for a non-display state, or a display position at which the identified medical image has been displayed.

19. The X-ray diagnostic apparatus according to claim 9, wherein the processing circuitry is configured to display the one medical image of the plurality of medical images in accordance with a kind of the identified medical image.

20. An X-ray diagnostic apparatus comprising:
- a storage configured to memorize a plurality of medical images;
- an imaging equipment including an X-ray tube configured to emit X-rays toward a subject and a detector configured to detect X-rays emitted from the X-ray tube;
- a display configured to display a plurality of medical images including X-ray images captured by the imaging equipment;
- an input interface configured to accept an operation instructing storage of one medical image of the plurality of medical images displayed on the display; and
- processing circuitry configured to identify, among the plurality of medical images, a medical image associated with an operation that includes at least one of operations related to image generation and image display and that was last-executed by an operator, among operations executed by the operator, and configured to cause the storage to memorize the identified medical image when the input interface has accepted the operation instructing storage of the one medical image of the plurality of medical images displayed on the display, wherein:
- the imaging equipment includes a first imaging system including a first X-ray tube configured to emit X-rays toward the subject and a first detector configured to detect X-rays emitted from the first X-ray tube and a second imaging system including a second X-ray tube configured to emit X-rays toward the subject and a second detector configured to detect X-rays emitted from the second X-ray tube;
- the display is configured to display a plurality of medical images including X-ray images captured by the first imaging system and a plurality of medical images including X-ray images captured by the second imaging system, respectively;
- the input interface is configured to accept an operation instructing storage of a medical image related to the first imaging system and a medical image related to the second imaging system displayed, respectively, on the display; and
- the processing circuitry is configured to identify, for medical images related to the first imaging system and medical images related to the second imaging system, each medical image associated with a last-executed operation, and to cause the storage to memorize the each of the identified medical images when the input interface has accepted an operation instructing storage of one medical image of the plurality of medical images related to the first imaging system and one medical image of the plurality of medical images of the second imaging system displayed on the display.

21. The X-ray diagnostic apparatus according to claim 20, wherein the input interface is configured to collectively or separately accept a first operation instructing storage of one medical image of the plurality of medical images related to the first imaging system and a second operation instructing storage of one medical image of the plurality of medical images related to the second imaging system.

* * * * *